United States Patent
Winter-Holt et al.

(10) Patent No.: US 10,604,524 B2
(45) Date of Patent: Mar. 31, 2020

(54) PYRROPYRIMIDINE COMPOUNDS AS MNKS INHIBITORS

(71) Applicant: LIFEARC, London (GB)

(72) Inventors: Jon James Winter-Holt, London (GB); Edward Giles Mciver, London (GB); Stephen Lewis, London (GB); Joanne Osborne, London (GB)

(73) Assignee: LIFE ARC, London (GB)

( * ) Notice: Subject to any disclaimer, the term of this patent is extended or adjusted under 35 U.S.C. 154(b) by 0 days.

(21) Appl. No.: 15/776,574

(22) PCT Filed: Nov. 16, 2016

(86) PCT No.: PCT/GB2016/053579
§ 371 (c)(1),
(2) Date: May 16, 2018

(87) PCT Pub. No.: WO2017/085483
PCT Pub. Date: May 26, 2017

(65) Prior Publication Data
US 2018/0346469 A1    Dec. 6, 2018

(30) Foreign Application Priority Data
Nov. 20, 2015    (GB) .................................... 1520499.3

(51) Int. Cl.
*C07D 487/04* (2006.01)
*A61K 31/519* (2006.01)
*A61K 45/06* (2006.01)

(52) U.S. Cl.
CPC .......... *C07D 487/04* (2013.01); *A61K 31/519* (2013.01); *A61K 45/06* (2013.01)

(58) Field of Classification Search
CPC ... A61K 31/519; A61K 45/06; A61K 2300/00
See application file for complete search history.

(56) References Cited

U.S. PATENT DOCUMENTS

| | | | |
|---|---|---|---|
| 8,754,079 B2 | 6/2014 | Lehmann-Lintz et al. | |
| 8,853,193 B2 | 10/2014 | Heckel et al. | |

(Continued)

FOREIGN PATENT DOCUMENTS

| | | | |
|---|---|---|---|
| CA | 2390948 A1 | 12/2000 | |
| WO | 84/03564 A1 | 9/1984 | |

(Continued)

OTHER PUBLICATIONS

Gangjee et al. (2012) "Novel Water-Soluble Substituted Pyrrolo [3,2-] pyrimidines: Design, Synthesis, and Biological Evaluation as Antitubulin Antitumor Agents," Pharmaceutical Research, Kluwer Academic Publishers—Plenum Publishers, NL, vol. 29, No. 11., pp. 3033-3039.
International Search Report of PCT/GB2016/053579 dated Jan. 4, 2017, 4 pp.
Berge et al. (1977) "Pharmaceutical Salts," Journal of Pharmaceutical Sciences, 66(1):21 pages.
Buxade et al. (2005) "The Mnks Are Novel Components in the Control of TNFalpha Biosynthesis and Phosphorylate and Regulate hmRNP A1," Immunity, 23:177-189.

(Continued)

*Primary Examiner* — Alexander R Pagano
*Assistant Examiner* — Ebenezer O Sackey
(74) *Attorney, Agent, or Firm* — Brian C. Trinque; Lathrop GPM LLP

(57) ABSTRACT

The present invention relates to compounds of formulae I, or pharmaceutically acceptable salts or esters thereof, wherein: $R_1$ is selected from H and CO—$NR_8R_9$, wherein $R_8$ and $R_9$ are each independently selected from H, alkyl, cycloalkyl and mono or bicyclic heterocycloalkyl, wherein said alkyl group is optionally substituted by one or more $R_{12}$ groups, and said heterocycloalkyl is optionally substituted by $R_{10}$ or $R_{12}$; or $R_8$ and $R_9$ are linked, together with the nitrogen to which they are attached, to form a heterocycloalkyl group optionally containing one or more additional heteroatoms, and optionally substituted by one or more groups select from $R_{10}$ and $(CH_2)_mR_{12}$; $R_2$ is selected from H and alkyl, wherein said alkyl group is optionally substituted by one or more $R_{12}$ groups; $R_3$ is selected from alkyl, cycloalkyl and heterocycloalkyl, each of which may be optionally substituted by halo, OH or alkoxy; $Z_1$, $Z_2$, $Z_3$ and $Z_4$ are all C; $R_4$, $R_5$, $R_6$ and $R_7$ are each independently selected from H, alkyl, CN, $NO_2$, OH, alkoxy, NHCO-alkyl, halo and haloalkyl; or $Z_1$, $Z_3$ and $Z_4$ are all C, $Z_2$ is N, $R_5$ is absent and $R_4$, $R_6$ and $R_7$ are as defined above; or $Z_1$, $Z_3$ and $Z_4$ are all C, $Z_1$ is N, $R_4$ is absent and $R_5$, $R_6$ and $R_7$ are as defined above; each $R_{10}$ and R11 is independently alkyl; each $R_{12}$ is independently selected from $CO_2R_{10}$, COOH, OH, alkoxy, haloalkyl, $NH_2$, $NHR_{10}$, $NR_{10}R_{11}$, heteroaryl and heterocycloalkyl; $R_{13}$ is H or halo. Further aspects relate to pharmaceutical compositions and therapeutic uses of said compounds in the treatment of diseases of uncontrolled cell growth, proliferation and/or survival, inappropriate cellular immune responses, inappropriate cellular inflammatory responses, or neurodegenerative disorders, preferably tauopathies, even more preferably, Alzheimer's disease.

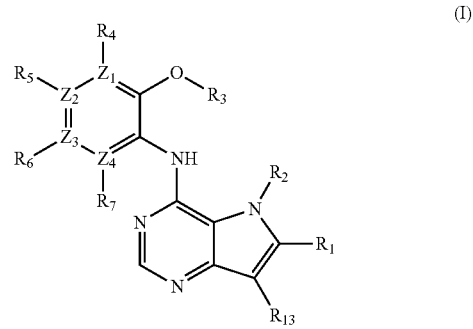

14 Claims, No Drawings

(56) References Cited

U.S. PATENT DOCUMENTS

| | | | |
|---|---|---|---|
| 2005/0153989 A1 | 7/2005 | Grotzfeld et al. | |
| 2010/0216788 A1* | 8/2010 | Ishikawa | C07D 487/04 514/234.2 |

FOREIGN PATENT DOCUMENTS

| | | |
|---|---|---|
| WO | 98/23613 A1 | 6/1998 |
| WO | 2006/014325 A2 | 2/2006 |
| WO | 2008006547 A2 | 1/2008 |
| WO | 2011104334 A1 * | 9/2011 |
| WO | 2011104334 A1 | 9/2011 |
| WO | 2014/118226 A1 | 8/2014 |
| WO | 2014/135480 A1 | 9/2014 |

OTHER PUBLICATIONS

Buxade et al. (2008) "The Mnks: MAP kinase-interacting kinasess (MAP kinase signal-integrating kinases)," Frontiers in Bioscience, 5359-5374.

Cherla et al. (2006) "Shiga toxin 1-induced cytokine production is mediated by MAP kinase pathways and translation initiation factor eIF4E in the macrophage-like THP-1 cell line," Journal of Leukocyte Biology, 79:397-407.

Chrestensen et al. (2007) "Loss of MNK function sensitizes fibroblasts to serum-withdrawal induced apoptosis," Genes to Cells, 12:1133-1140.

Fingl et al. (1975) Introduction, Generak Principles, The Pharmacological Basis of Therapeutics, Chapter 1, 46 pages.

Gennaro, Alfonso R., (1985) Remington's Pharmaceutical Sciences, 17th Edition, 9 pages.

Jauch et al., (2006) "Mitogen-activated protein kinases interacting kinases are autoinhibited by a reprogrammed activation segment," The EMBO Journal, 25:4020-4032.

Kjellerup et al. (2008) "Pro-inflammatory cytokine release in keratinocytes is mediated through the MAPK signal-intergrating kinases," Experimental Dermatology, 17:498-504.

Konicek et al. (2008) "Targeting the eIF4F translation initiation complex for cancer therapy," Cell Cycle, 7 (16):2466-2471.

Konicek et al. (2011) "Therapeutic Inhibition of MAP Kinase Interacting Kinase Blocks Eukaryotic Initiation Factor 4E Phosphorylation and Suppresses Outgrowth of Experimental Lung Metastases," Cancer Res., 71(5):1849-1857.

March, Jerry (1985) Advanced Organic Chemistry, Third Edition, 5 pages.

Nikolcheva et al., "A translational rheostat for RFLAT-1 regulates RANTES expression inT lymphocytes," J. Clin. Invest., 110:119-126.

Noubade et al. (2011) "Activation of p38 in CD4 T cells controls IL-17 production and autoimmune encephalomyelitis," Blood, 118(12):3290-3300.

Rowlett et al. (2008) "MNK kinases regulate multiple TLR pathways and innate proinflammatory cytokines in macrophages," Am. J. Physiol. Gastrointest. Liver Physiol., 294:G452-G459.

Teo et al., (2015) "Pharmacologic Inhibition of MNKs in Acute Myeloid Leukemia," Molecular Pharmacology, 88:380-389.

Teo et al., (2015) "Pharmacologic co-inhibition of MNKs and mTORC1 synergistically suppresses proliferation and perturbs cell cycle progression in blast crisis-chronic myeloid leukemia cells," Cancer Letters, 357:612-623.

Ueda et al., (2010) "Combined deficiency for MAP kinase-interacting kinase 1 and 2 (Mnk1 and Mnk2) delays tumor development," PNAS, 107(32):13984-13990.

Wade et al. (1994) Handbook of Pharmaceutical Excipients, Second Edition.

Wendel et al. (2007) "Dissecting eIF4E action in tumorigenesis," Genes and Development, 21:3232-3237.

* cited by examiner

PYRROPYRIMIDINE COMPOUNDS AS MNKS INHIBITORS

CROSS-REFERENCE TO RELATED APPLICATIONS

This application is a 35 U.S.C. § 371 filing of International Application No. PCT/GB2016/053579, filed on Nov. 16, 2016, which claims priority to Great Britain patent application number 1520499.3, filed Nov. 20, 2015. The entire contents of these applications are incorporated by reference herein, in their entirety.

FIELD OF THE INVENTION

The present invention relates to fused pyrrolopyrimidine compounds that are capable of inhibiting one or more kinases, more particularly, MAP kinase-interacting serine/threonine-protein kinases (MNKs). The compounds have potential therapeutic applications in the treatment of a variety of disorders, including proliferative disorders, and neurodegenerative diseases such as Alzheimer's disease.

BACKGROUND TO THE INVENTION

The present invention relates to chemical compounds that inhibit the enzymatic activity of MAP kinase-interacting serine/threonine-protein kinases (MNKs). MNK proteins are encoded by the two genes MKNK1 and MKNK2 which give rise to MNK1 and 2. Both proteins come in two isoforms generated by alternative splicing. The shorter isoform, referred to as MNK1b/2b, lacks the MAP kinase binding domain which results in low basal activity (Buxade et al. Front Biosci 2008, 5359-5373). Mnk1a is activated through ERK and p38 but not JNK binding, whereas MNK2a appears to be only activated by ERK.

The catalytic domains of MNK1 and 2 are very similar. The domains are, however, very distinct from other kinases as they display a DFD motif in the ATP binding site instead of the typical DFG motif, which suggests an altered activation loop confirmation (Jauch et al. EMBO J 2006, 4020-4032). MNK1/2 are ubiquitously expressed with phosphorylate eukaryotic initiation factor 4E (eIF4E), cytoplasmic phospholipase A2 (cPLA2) heterogeneous nuclear RNA-binding protein A1 (hnRNP A1), polypyrimidine-tract binding protein-associated splicing factors (PSF) and Sprouty 2 (hSPRY2) (Buxade et al. Front Biosci 2008, 5359-5373).

MNKs have been linked to cancer through the phosphorylation of eIF4E. eIF4E is an oncogene which is amplified in cancer and is solely phosphorylated by MNKs (Konicek et al. Cell Cycle 2008, 2466-2471). eIF4E overexpression induces tumour formation in animals models. Increased phosphorylation of eIF4E has been observed in many solid tumours and lymph node metastasis where it correlates with poor prognosis. eIF4E is the rate limiting factor in cap-dependent translation where it directs ribosomes to the cap structure of mRNA-freely or as part of the eIF4F pre-initiation complex. Almost all proteins require eIF4E for translation. Phosphorylation of eIF4E leads to preferred translation of mRNA involved in cell survival, angiogenesis and cancer metastasis, such as mRNA for cyclin D1, Myc, Mcl-1, Bcl-2 and VEGF. These mRNAs are usually less efficiently translated due to long and complex 5'UTRs. Phosphorylation of eIF4 does not affect the overall translation rate but has been suggested to aid polysome formation, which facilitates more efficient translation.

A number of MNK1/MNK2 inhibitors are known in the art. For example, U.S. Pat. Nos. 8,754,079 and 8,853,193 (both in the name of Boehringer Ingelheim International GMBH) disclose thienopyrimidine compounds that are capable of inhibiting MNK1 and/or MNK2. Likewise, WO 2014/135480 (Bayer Pharma Aktiengesellschaft) discloses thiazolopyrimidines substituted by an indazolyl or 2-oxo-2,3,dihydro-1,3-benzothiazolyl group. WO 2014/118226 (Bayer Pharma Aktiengesellschaft) discloses substituted pyrazolylopyrimidinylamino-indazoles that are capable of inhibiting MNK1 and/or MNK2.

The present invention seeks to provide alternative compounds that are capable of interfering with the activity of MNK and its pathways. Such compounds have potential therapeutic applications in the treatment of a variety of disorders, including proliferative disorders and neurodegenerative disorders.

STATEMENT OF INVENTION

A first aspect of the invention relates to a compound of formula (I), or a pharmaceutically acceptable salt or ester thereof,

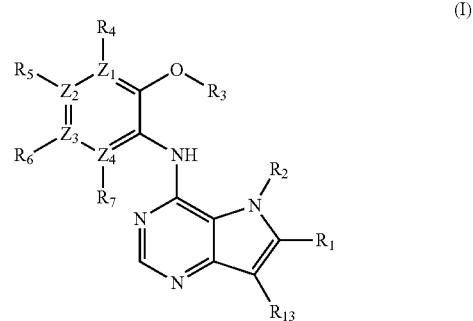

(I)

wherein:
  $R_1$ is selected from:
  H;
  CO—$NR_8R_9$, wherein $R_8$ and $R_9$ are each independently selected from H, alkyl, cycloalkyl and mono or bicyclic heterocycloalkyl, wherein said alkyl group is optionally substituted by one or more $R_{12}$ groups, and said heterocycloalkyl is optionally substituted by one or more groups selected from $R_{10}$ and $R_{12}$; or $R_8$ and $R_9$ are linked, together with the nitrogen to which they are attached, to form a heterocycloalkyl group optionally containing one or more additional heteroatoms, and optionally substituted by one or more groups select from $R_{10}$ and $(CH_2)_m R_{12}$;
  $R_2$ is selected from H and alkyl, wherein said alkyl group is optionally substituted by one or more $R_{12}$ groups;
  $R_3$ is selected from alkyl, cycloalkyl and heterocycloalkyl, each of which may be optionally substituted by one or more groups selected from halo, OH and alkoxy;
  $Z_1$, $Z_2$, $Z_3$ and $Z_4$ are all C;
  $R_4$, $R_5$, $R_6$ and $R_7$ are each independently selected from H, alkyl, CN, $NO_2$, OH, alkoxy, NHCO-alkyl, halo and haloalkyl; or
  $Z_1$, $Z_3$ and $Z_4$ are all C, $Z_2$ is N, $R_5$ is absent and $R_4$, $R_6$ and $R_7$ are as defined above; or
  $Z_2$, $Z_3$, and $Z_4$ are all C, $Z_1$ is N, $R_4$ is absent and $R_5$, $R_6$ and $R_7$ are as defined above;
  each $R_{10}$ and $R_{11}$ is independently alkyl;

each $R_{12}$ is independently selected from $CO_2R_{10}$, COOH, OH, alkoxy, haloalkyl, $NH_2$, $NHR_{10}$, $NR_{10}R_{11}$, heteroaryl and heterocycloalkyl, wherein said heterocycloalkyl is optionally further substituted by one or more $R_{10}$ groups;

$R_{13}$ is H or halo.

Advantageously, the presently claimed compounds are capable of inhibiting MNK1 and/or MNK2. Moreover, in one embodiment, the presently claimed compounds advantageously exhibit improved selectivity for MNK1 and/or MNK2 over other kinases when compared to compounds known in the art.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating a proliferative disorder.

A fifth aspect of the invention relates to a compound as described above for use in treating a neurodegenerative disease such as Alzheimer's Disease.

A sixth aspect of the invention relates to the use of a compound as described above in the preparation of a medicament for treating or preventing a prolferative disorder, or a neurodegenerative disease.

As seventh aspect of the invention relates to the use of a compound as described above in the preparation of a medicament for the prevention or treatment of a disorder caused by, associated with or accompanied by any abnormal kinase activity, wherein the kinase is preferably MNK.

An eighth aspect of the invention relates to a method of treating a mammal having a disease state alleviated by inhibition of a kinase (preferably MNK), wherein the method comprises administering to a mammal a therapeutically effective amount of a compound as described above.

A ninth aspect of the invention relates to the use of a compound as described above in an assay for identifying further candidate compounds capable of inhibiting a kinase, preferably MNK.

DETAILED DESCRIPTION

The present invention relates to fused pyrrolopyrimidine compounds that are capable of inhibiting one or more kinases, more particularly MNK.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

"Heterocycloalkyl" refers to a monocyclic or bicyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

In one preferred embodiment, each $R_{12}$ is independently selected from OH, alkoxy, haloalkyl, $NH_2$, $NHR_{10}$, $NR_{10}R_{11}$, and heterocycloalkyl, wherein said heterocycloalkyl is optionally further substituted by one or more $R_{10}$ groups.

In one preferred embodiment:
$Z_1$, $Z_2$, $Z_3$ and $Z_4$ are all C; and
$R_4$, $R_5$, $R_6$ and $R_7$ are each independently selected from H, alkyl, alkoxy, and halo.

In one preferred embodiment:
$Z_1$, $Z_2$, $Z_3$ and $Z_4$ are all C;
$R_4$, $R_5$, $R_6$ and $R_7$ are all H; or
$R_4$, $R_6$ and $R_7$ are all H and $R_5$ is halo.

In one preferred embodiment, $Z_1$, $Z_2$, $Z_3$ and $Z_4$ are all C, $R_4$, $R_6$ and $R_7$ are all H, and $R_5$ is fluoro.

In one preferred embodiment:
$Z_1$ is N, and $Z_2$, $Z_3$ and $Z_4$ are all C;
$R_4$ is absent, and $R_5$, $R_6$ and $R_7$ are all H or halo.

In one preferred embodiment, $R_3$ is selected from alkyl, cyclopropyl, cyclobutyl, cyclopentyl, tetrahydrofuranyl and tetrahydropyranyl, each of which may be optionally substituted by one or more groups selected from fluoro, OH and methoxy.

In one preferred embodiment, $R_3$ is alkyl, more preferably, isopropyl.

In one highly preferred embodiment, $Z_1$, $Z_2$, $Z_3$ and $Z_4$ are all C, $R_4$, $R_6$ and $R_7$ are all H, and $R_8$ is fluoro, and $R_3$ is isopropyl.

In one highly preferred embodiment, $R_1$ is H.

In one preferred embodiment, $R_1$ is CO—$NR_8R_9$, wherein $R_8$ and $R_9$ are each independently selected from H, alkyl, cycloalkyl and mono or bicyclic heterocycloalkyl, wherein said alkyl group is optionally substituted by one or more $R_{12}$ groups, and said heterocycloalkyl is optionally substituted by one or more groups selected from $R_{10}$ and $R_{12}$.

In a more preferred embodiment, $R_1$ is CO—$NR_8R_9$ wherein one of $R_8$ and $R_9$ is H, and the other is alkyl optionally substituted by one or more groups selected from $NR_{10}R_{11}$ and heterocycloalkyl, wherein said heterocycloalkyl is optionally substituted by one or more $R_{10}$ groups. Preferably, the heterocycloalkyl is piperidinyl or piperazinyl, each of which is optionally substituted by one or more $R_{10}$ groups.

In one highly preferred embodiment, $R_1$ is CO—$NR_8R_9$ wherein one of $R_8$ and $R_9$ is H, and the other is alkyl optionally substituted by $NMe_2$.

In one preferred embodiment, $R_2$ is selected from H and alkyl, wherein said alkyl is optionally substituted by one or more groups selected from OH and alkoxy.

In a more preferred embodiment, $R_2$ is selected from H, methyl, ethyl, isopropyl, hydroxyethyl and methoxyethyl.

In a more preferred embodiment, R$_{13}$ is H or Cl, more preferably, H.
In one embodiment, the compound of the invention is selected from the following:
1
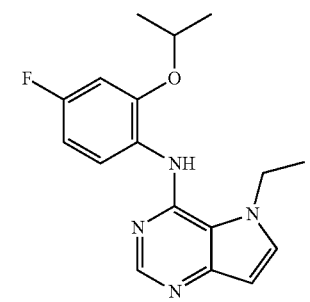
2
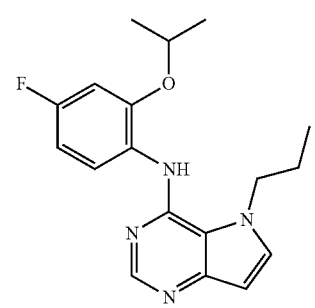
3
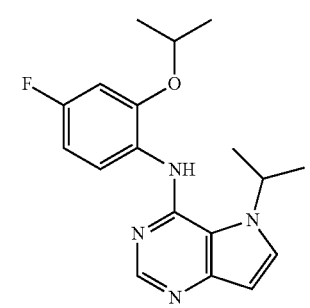
4
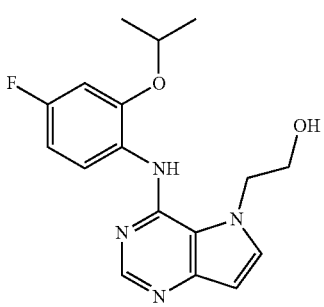
5
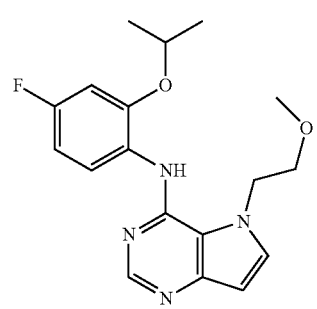
-continued
6
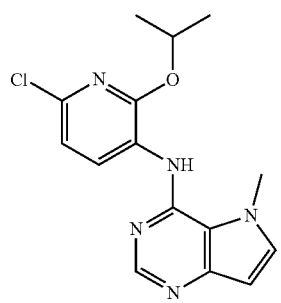
7
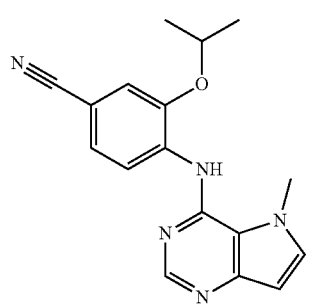
8
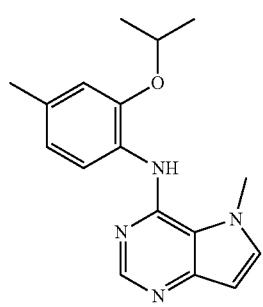
9
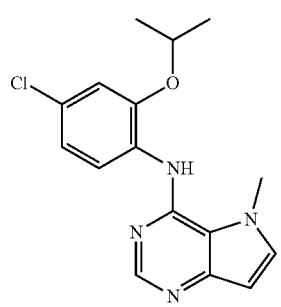
10
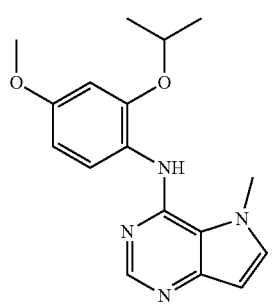

-continued
11
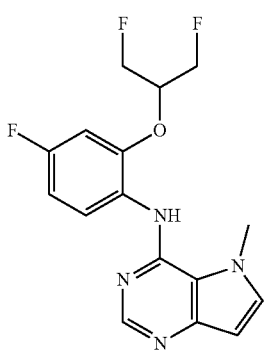
AND Enantiomer
12
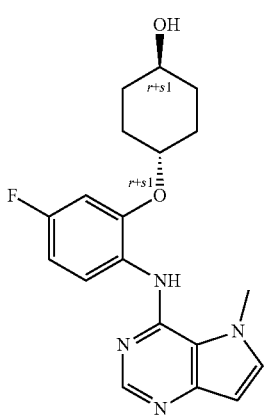
13
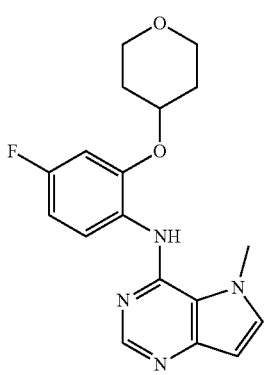
14
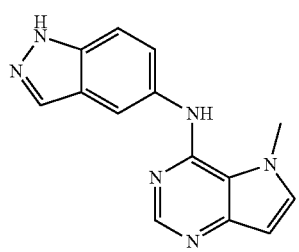
15
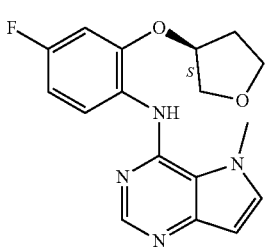
-continued
16
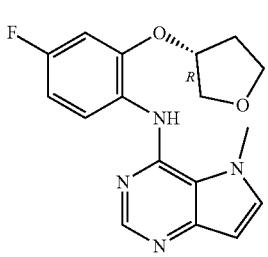
17
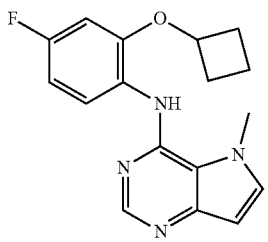
18
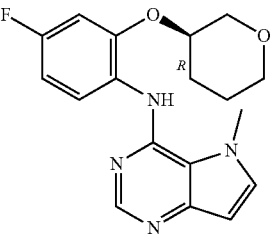
19
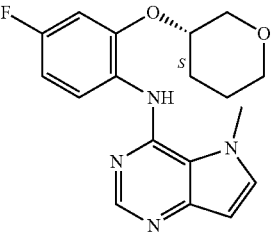
20
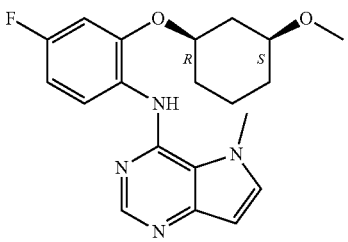
21
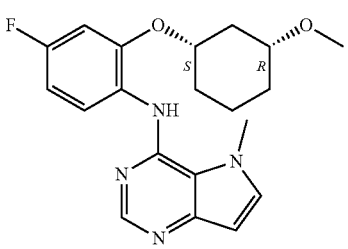

-continued

| 22 |
| 23 |
| 24 |
| 25 |
| 26 |
| 27 |
| 28 |
| 29 |
| 30 |
| 31 |
| 32 |

-continued

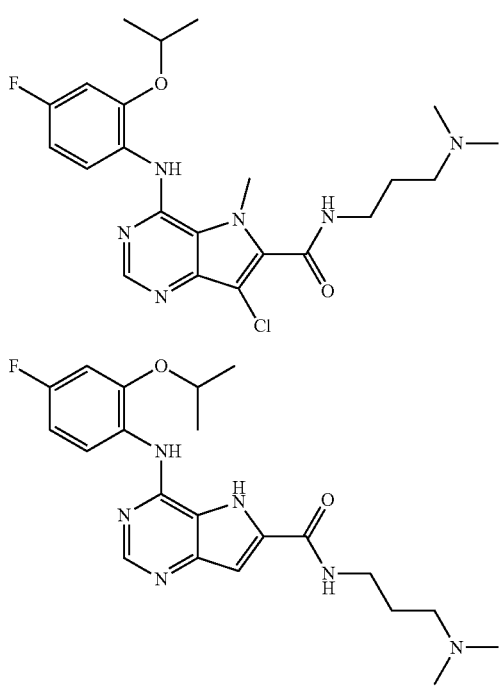

and pharmaceutically acceptable salts thereof.

Therapeutic Applications

A further aspect of the invention relates to a compound as described above for use in medicine.

Another aspect of the invention relates to a compound as described above for use in treating a proliferative disorder.

In one preferred aspect, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the MKNK-1 pathway.

In one preferred embodiment, the disease of uncontrolled cell growth, proliferation and/or survival, inappropriate cellular immune response, or inappropriate cellular inflammatory response is a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

As MNKs are the only kinases known to phosphorylate eIF4E, inhibition of eIF4E phosphorylation through inhibition of MNKs is expected to negatively affect these pathways and hence interfere with progression of cancer and metastases. Surprisingly, MNK1/2 double KO mice show no overt phenotype, which is unexpected given the central role of eIF4E. Still, MNK phosphorylation of eIF4E on Serin 209 is believed to be important for eIF4E's oncogenic activity as overexpression of constitutively active MNK1 but not kinase-inactive MNK1 was shown to accelerate tumour formation in mouse embryonic fibroblasts (Chrestensen et al. Genes Cells 2007, 1133-1140). Constitutively active MNK1 but not kinase dead was also shown to promote tumour growth in an Ep-Myc transgenic model in hematopoietic stem cells. Vice versa, deficiency of MNKs (double KO) was found to delay the development of tumours in a lymphoma model induced by the loss of PTEN (Ueda et al. Proc Nati Acad Sci USA 2010, 13984-13990). This is in line with results obtained using mutated forms of eIF4E. eIF4E S209D mimics the phosphorylated version eIF4E and eIF4E S209A cannot be phosphorylated. Mice reconstituted with cells expressing the S209A mutant were defective at promoting tumorigenesis. By contrast, mice reconstituted with cells expressing the phosphomimetic S209D mutant displayed accelerated tumor onset (Wendel et al. Genes Dev 2007, 3232-3237).

Pharmacological inhibition of MNK using anti-fungal agent cercosporamide was shown to effectively block eIF4E phosphorylation within 30 minutes after oral administration in normal mouse tissues and xenografted tumors, reducing tumor growth in HCT116 xenograft models, and suppressing the outgrowth of B16 melanoma lung metastases. Collectively, these data substantiate the notion that blocking Mnk function, and eIF4E phosphorylation, may be an attractive anticancer strategy (Konicek et al. Cancer Res 2011, 1849-1857). This notion has been further supported by the use of more specific MNK inhibitory compounds in cellular models of leukemia, where MNK inhibitors were shown to have an anti-proliferative effect (Tea et al. Mol Pharmacol 2015, 380-389, Teo et al. Cancer Lett 2015, 612-623).

In addition to cancer MNKs are promising targets for anti-inflammatory therapy. MNKs were shown to be involved in regulating TNF-production on a post transcriptional level. TNF expression is controlled via AU-rich elements in the 3'UTR of its mRNA. MNK inhibition or knockdown of MNK1 was shown to inhibit TNF production in Jurkat cells, whereas overexpression of the 3'UTR of TNF enhanced the expression of a reporter construct (Buxade et al. Immunity 2005, 177-189). In the macrophage cell line RAW264.7 stimulation with different TLR agonists, LPS or CpG DNA in presence of MNK inhibitor reduced TNF production, correlating with an increase in TNF mRNA decay (Rowlett et al. Am J Physiol Gastrointest Liver Physiol 2008, G452-459). In BMDMs isolated from a spontaneous mouse model of Crohn's disease-like ileitis, treatment with MNK inhibitor inhibited production of TNF and IL-6. A study in the monocytic cell line THP-1 showed that the release of IL-1β and IL-8 induced by Shiga toxin could be blocked by MNK inhibitor CGP57380 by 73-96% (Cherla et al. J Leukoc Biol 2006, 397-407). In neutrophils, it was shown that MNK plays a role in the activation of neutrophils in response to LPS and TNF stimulation. MNK inhibition not only affected cytokine production by neutrophils but also inhibited the anti-apoptotic effect of TNF and LPS on neutrophils.

Another study shows reduced TNF-production in keratinocytes in the presence of MNK inhibitor CGP57380 along with decreased expression of IL-1β and IL-6, thereby implicating MNK in regulation of pro-inflammatory cytokine expression in inflammatory skin diseases (Kjellerup et al. Exp Dermatol 2008, 498-504). Interleukin 17 is pro-inflammatory cytokine that acts synergistically with TNF and IL-1β. In murine CD4 T cells which were activated under Th17 conditions in the presence of MNK inhibitor, blockage of eIF-4E phosphorylation was detected, resulting in reduced IL-17 production without affecting IL-17 mRNA (Noubade et al. Blood 2011, 3290-3300). RANTES, which is a chemokine involved in the terminal differentiation of T cells was found to be indirectly regulated by MNK via its major transcriptional regulator RFLAT1. Inhibition of MNK was shown to reduce RFLAT1 production (Nikolcheva et al. J Clin Invest 2002, 119-126).

Another aspect of the invention relates to a compound as described above for use in treating a neurodegenerative disorder, more preferably a tauopathy.

Tauopathies are a class of neurodegenerative diseases associated with the pathological aggregation of tau protein-in the human brain. The best-known of these illnesses is Alzheimer's disease (AD), wherein tau protein is deposited within neurons in the form of neurofibrillary tangles (NFTs). Tangles are formed by hyperphosphorylation of a microtubule-associated protein known as tau, causing it to aggregate in an insoluble form. These aggregations of hyperphosphorylated tau protein are also referred to as PHF, or "paired helical filaments".

In one preferred embodiment of the invention, the tauopathy is Alzheimer's disease.

Another aspect relates to the use of a compound as described above in the preparation of a medicament for treating or preventing a neurodegenerative disorder. Preferably, the neurodegenerative disorder is Alzheimer's Disease.

Another aspect relates to the use of a compound as described above in the preparation of a medicament for treating or preventing a proliferative disorder, preferably cancer or leukemia.

Preferably, the compound is administered in an amount sufficient to inhibit one or more kinases, preferably MNK 1 and/or MNK2.

In one preferred embodiment, the compound is administered in an amount to inihibit MNK1.

In one preferred embodiment, the compound is administered in an amount to inihibit MNK2.

Yet another aspect relates to the use of a compound of the invention in the preparation of a medicament for the prevention or treatment of a disorder caused by, associated with or accompanied by any abnormal activity against a biological target, wherein the target is a kinase, more preferably MNK.

Another aspect of the invention relates to a method of treating a protein kinase related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of a protein kinase, wherein the method comprises administering to a mammal a therapeutically effective amount of a compound according to the invention.

Preferably, the disease state is alleviated by the inhibition of the protein kinase MNK.

Preferably, the mammal is a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a protein kinase together in such a manner that the compound can affect the enzyme activity of the protein kinase either directly; i.e., by interacting with the protein kinase itself or indirectly; i.e., by interacting with another molecule on which the catalytic activity of the protein kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "kinase related disease or disorder" refers to a disease or disorder characterized by inappropriate kinase activity or over-activity of a kinase as defined herein.

Inappropriate activity refers to either; (i) kinase expression in cells which normally do not express said kinase; (ii) increased kinase expression leading to unwanted cell proliferation, differentiation and/or growth; or, (iii) decreased kinase expression leading to unwanted reductions in cell proliferation, differentiation and/or growth. Over-activity of kinase refers to either amplification of the gene encoding a particular kinase or production of a level of kinase activity, which can correlate with a cell proliferation, differentiation and/or growth disorder (that is, as the level of the kinase increases, the severity of one or more of the symptoms of the cellular disorder increases). Over activity can also be the result of ligand independent or constitutive activation as a result of mutations such as deletions of a fragment of a kinase responsible for ligand binding.

Preferred diseases or disorders that the compounds described herein may be useful in preventing, include neurodegenerative disorders such as Alzheimer's Disease, and proliferative disorders, such as cancer.

Thus, the present invention further provides use of compounds as defined herein for the manufacture of medicaments for the treatment of diseases where it is desirable to inhibit MNK. Such diseases include proliferative disorders and neurodegenerative disorders such as Alzheimer's Disease, as described above.

Pharmaceutical Compositions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivalate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, made and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of the invention may be administered to inhibit the kinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mglkg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e.

before, simultaneously, or after delivery. Such scheduling may be a feature of all the active agents identified herein.

In one preferred embodiment, the additional active agent is selected from an antidiabetic agent, a lipid lowering agent, a cardiovascular agent, an antihypertensive agent, a diuretic agent, a thrombocyte aggregation inhibitor, an antineoplastic agent and an anti-obesity agent.

In one preferred embodiment, the additional active agent is selected from a histamine antagonist, a bradikinin antagonist, serotonin antagonist, leukotriene, an anti-astinnatic, an NSAID, an antipyretic, a corticosteroid, an antibiotic, an analgetic, a uricosuric agent chemotherapeutic agent, an anti gout agent, a bronchodilator, a cyclooxygenase-2 inhibitor, a steroid, a 5-lipoxygenase inhibitor, an innmmosuppressive agent, a leukotriene antagonist, a cytostatic agent, an antineoplastic agent, am Tor inhibitor, a Tyrosine kinase inhibitor, antibodies or fragments thereof against cytokines and soluble parts (fragments) of cytokine receptors.

Assay

A further aspect of the invention relates to the use of a compound as described above in an assay for identifying further candidate compounds capable of inhibiting one or more kinases, more preferably MNK.

Preferably, the assay is a competitive binding assay.

More preferably, the competitive binding assay comprises contacting a compound of the invention with a kinase, preferably MNK, and a candidate compound and detecting any change in the interaction between the compound according to the invention and the kinase.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to a kinase, said method comprising the steps of:
(i) contacting a ligand with a kinase in the presence of a known substrate of said kinase;
(ii) detecting any change in the interaction between said kinase and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove. Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders as described above.

The above methods may be used to screen for a ligand useful as an inhibitor of one or more kinases.

Compounds of the invention are useful both as laboratory tools and as therapeutic agents. In the laboratory certain compounds of the invention are useful in establishing whether a known or newly discovered kinase contributes a critical or at least significant biochemical function during the establishment or progression of a disease state, a process commonly referred to as 'target validation'.

The present invention is further described by way of the following non-limiting examples.

EXAMPLES

General Procedures for Synthesis of Compounds

Chromatography

Preparative high pressure liquid chromatography was carried out using apparatus made by Agilent. The apparatus is constructed such that the chromatography is monitored by a multi-wavelength UV detector (G1365B manufactured by Agilent) and an MM-ES+APCI mass spectrometer (G-1956A, manufactured by Agilent) connected in series, and if the appropriate criteria are met the sample is collected by an automated fraction collector (G1364B manufactured by Agilent). Collection can be triggered by any combination of UV or mass spectrometry or can be based on time. Typical conditions for the separation process are as follows: Chromatography column was an Xbridge C-18 (19×100 mm); the gradient was run over a 7 minute period at a flow rate of 40 ml/min (gradient at start: 10% methanol and 90% water, gradient at finish: 100% methanol and 0% water; as buffer: either 0.1% formic acid, 0.1% ammonium hydroxide or 0.1% trifluoroacetic acid was added to the water). It will be appreciated by those skilled in the art that it may be necessary or desirable to modify the conditions for each specific compound, for example by changing the solvent composition at the start or at the end, modifying the solvents or buffers, changing the run time, changing the flow rate and/or the chromatography column.

Flash chromatography refers to silica gel chromatography and carried out using an SP4 or an Isolara 4 MPLC system (manufactured by Biotage); pre-packed silica gel cartridges (supplied by Biotage); or using conventional glass column chromatography.

Analytical Methods $^1$H Nuclear magnetic resonance (NMR) spectroscopy was carried out using an ECX400 spectrometer (manufactured by JEOL) in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; br, broad.

Analytical LCMS was typically carried out using an Agilent HPLC instrument with C-18 Xbridge column (3.5 μm, 4.6×30 mm, gradient at start: 10% organic phase and 90% water, gradient at finish: organic and 0% water; as buffer: either 0.1% ammonium hydroxide or 0.1% trifluoroacetic acid was added to the water). The organic solvent was either acetonitrile or methanol. A flow rate of 3 mL/min was used with UV detection at 254 and 210 nm.

Mass spectra were recorded using a MM-ES+APCI mass spectrometer (G-1956A, manufactured by Agilent). Where thin layer chromatography (TLC) has been used it refers to silica gel TLC using silica gel MK6F 60 Å plates, $R_f$ is the distance travelled by the compound divided by the distance travelled by the solvent on a TLC plate.

Compound Preparation

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

Where reactions are carried out using microwave irradiation, the microwave used is an Initiator 60 supplied by Biotage. The actual power supplied varies during the course of the reaction in order to maintain a constant temperature.

Some hydrogenations were carried out using an H-Cube® Continuous-flow Hydrogenation Reactor manufactured by ThalesNano. The catalysts are supplied by ThalesNano as cartridges "CatCarts" The pressure, flow rate, temperature and cartridge are indicated in the experimantal section. The equipment was used in accordance with the manufacturer operating procedure. The person skilled in the art will appreciate that it may be necessary or desirable to run repeat cycles of the reaction mixture and in some instances, replace the cartridge between cycles to improve the yield of the reaction.

Abbreviations

A list of some common abbreviations are shown below—where other abbreviations are used which are not listed, these will be understood by the person skilled in the art.

DCM=Dichloromethane
DMF=N,N-Dimethylformamide
THF=Tetrahydrofuran
MeOH=Methanol
TFA=Trifluoroacetic acid
Xantphos=4,5-Bis(diphenylphosphino)-9,9-dimethylxanthene
HATU=N,N,N',N'-Tetramethyl-O-(7-azabenzotriazol-1-yl) uronium-hexafluorophospate
EDCI=1,3-Propanediamine, N3-(ethylcarbonimidoyl)-N1, N1-dimethyl-, hydrochloride
DCC=1,3-Dicyclohexylcarbodiimide
Pd$_2$(dba)$_3$=tris(dibenzylideneacetone)dipalladium(0)
TEA=Triethylamine
rm=Reaction mixture
rt=Room temperature
AcOH=Acetic acid
IPA=Isopropanol
DIPEA=N,N-diisopropylethylamine
TBSMSCl=Tertiarybutyldimethylsilyl chloride
MeCN=Acetonitrile
NH$_3$=Ammonia
EtOH=Ethanol
EtOAc=Ethyl Acetate
LCMS=Mass spectrometry directed high pressure liquid chromatography
UV=Ultraviolet
SCX=Strong cation exchange
TPAP=Tetrapropylammonium perruthenate
DMSO=Dimethylsulphoxide
BINAP=2,2'-bis(diphenylphosphino)-1,1'-binaphthyl
TPAP=Tetrapropylammonium perruthenate
DIAD=Diisopropyl azodicarboxylate
NMO=N-Methylmorpholine N-oxide Intermediate 1

4-Chloro-5-methyl-pyrrolo[3,2-d]pyrimidine

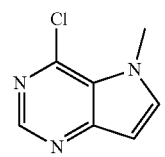

To a solution of sodium hydride (60% dispersion in mineral oil) (1.625 g, 42 mmol) in THF (75 ml), at 0° C., was added 4-chloro-5H-pyrrolo [3,2-d]pyrimidine (5 g, 32 mmol) and stirred for 1 hour. Iodomethane (3.046 ml, 49 mmol) was added and the mixture stirred overnight. The mixture was concentrated, taken up in EtOAc and washed with water. The organic layer was separated, dried and concentrated to an orange solid (4.63 g, 85%); $^1$H NMR (400 MHz, DMSO-d$_6$) δ ppm 4.07 (s, 3H), 6.66 (d, J=3.20 Hz, 1H), 7.94 (d, J=3.21 Hz, 1H), 8.56 (s, 1H); LC-MS (ESI): (MH$^+$) 168/170.

Intermediate 2

4-Chloro-5-ethylpyrrolo[3,2-d]pyrimidine

To a solution of 4-chloro-5H-pyrrolo[3,2-d]pyrimidine (150 mg, 0.98 mmol) and caesium carbonate (637 mg, 1.96 mmol) in DMF (5 ml) was added bromoethane (128 mg, 1.18 mmol) and stirred overnight. The mixture was diluted with EtOAc and washed with water (×3). The organic phase was separated, dried and concentrated to give a brown solid (156 mg, 88%); $^1$H NMR (400 MHz, CHLOROFORM-d) δ ppm 1.46 (t, J=7.3 Hz, 3H), 4.50 (q, J=6.9 Hz, 2H), 6.66 (d, J=3.2 Hz, 1H), 7.47 (d, J=3.2 Hz, 1H), 8.63 (s, 1H); LC-MS (ESI): (MH$^+$) 182/184

Intermediate 3

4-Chloro-5-propyl-pyrrolo[3,2-d]pyrimidine

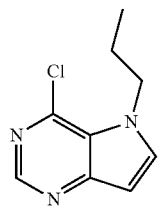

Intermediate 3 was prepared analogously to Intermediate 2 with 4-chloro-5H-pyrrolo[3,2-d]pyrimidine and 1-bromopropane to give 4-ohloro-5-propyl-pyrrolo[3,2-d]pyrimidine (69% yield); $^1$H NMR (400 MHz, CHLOROFORM-d) δ ppm 0.96 (t, J=7.3 Hz, 3H), 1.92 (sxt, J=7.3 Hz, 2H), 4.45 (t, J=7.3 Hz, 2H), 6.72 (d, J=3.2 Hz, 1H), 7.49 (d, J=3.2 Hz, 1H), 8.70 (s, 1H); LC-MS (ESI): (MH$^+$) 196/198

Intermediate 4

4-Chloro-5-isopropyl-pyrrolo[3,2-d]pyrimidine

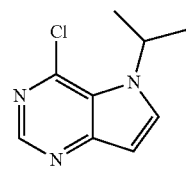

Intermediate 4 was prepared analogously to Intermediate 2 with 4-chloro-5H-pyrrolo[3,2-d]pyrimidine and 2-bromopropane to give 4-chloro-5-isopropyl-pyrrolo[3,2-d]pyrimidine (63% yield); $^1$H NMR (400 MHz, CHLOROFORM-d) δ ppm 1.57 (d, J=6.0 Hz, 6H), 5.50 (spt, J=6.9 Hz, 1H), 6.72-6.78 (m, 1H), 7.69 (d, J=3.6 Hz, 1H), 8.70 (s, 1H); LC-MS (ESI): (MH$^+$) 196/198

Intermediate 5

2-(4-Chloropyrrolo[3,2-d]pyrimidin-5-yl)ethanol

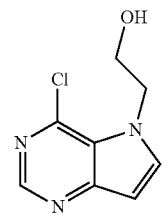 [SMILES: OCCn1ccc2ncnc(Cl)c21]

Intermediate 5 was prepared analogously to Intermediate 2 with 4-chloro-5H-pyrrolo[3,2-d]pyrimidine and 2-bromoethanol to give 2-(4-chloropyrrolo[3,2-d]pyrimidin-5-yl)ethanol (37% yield); $^1$H NMR (400 MHz, Solvent) δ ppm 3.89 (t, J=5.5 Hz, 2H), 4.64 (t, J=5.5 Hz, 2H), 6.69 (d, J=3.2 Hz, 1H), 7.86 (d, J=3.2 Hz, 1H), 8.56 (s, 1H); LC-MS (ESI): (MH$^+$) 198/200

Intermediate 6

4-Chloro-5-(2-methoxyethyl)pyrrolo[3,2-d]pyrimidine

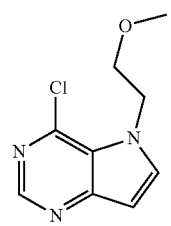

Intermediate 6 was prepared analogously to Intermediate 2 with 4-chloro-5H-pyrrolo[3,2-d]pyrimidine and 2-bromoethyl methyl ether to give 4-chloro-5-(2-methoxyethyl)pyrrolo[3,2-d]pyrimidine, which was used in the next step without further purification (MH$^+$) 212/214

Intermediate 7

3-Isopropoxy-4-nitrobenzonitrile

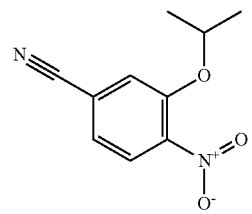

To a solution of IPA (1.01 ml, 13.3 mmol) in THF (150 ml), at 0° C., was added LiHMDS (1M THF) (14.4 ml, 14.4 mmol) and stirred for 1 hour. 3-Fluoro-4-nitrobenzonitrile (2 g, 12.0 mmol) was added and the mixture stirred overnight. DCM and water were added, the organic layer separated, dried and concentrated to give an orange solid (2.42 g, 98%); $^1$H NMR (400 MHz, CHLOROFORM-d) δ ppm 1.43 (d, J=6.00 Hz, 6H), 4.71 (spt, J=6.03 Hz, 1H), 7.28-7.32 (m, 1H), 7.33-7.37 (m, 1H), 7.80 (d, J=8.20 Hz, 1H)

Intermediate 8

2-Isopropoxy-4-methyl-1-nitro-benzene

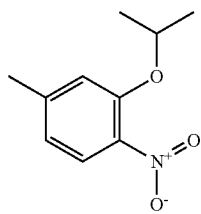

Intermediate 8 was prepared analogously to Intermediate 7 with 2-fluoro-4-methyl-nitrobenzene to give 2-isopropoxy-4-methyl-1-nitro-benzene; 53% yield; $^1$H NMR (400 MHz, CHLOROFORM-d) δ ppm 1.40 (d, J=6.0 Hz, 6H), 2.40 (s, 3H), 4.66 (spt, J=6.0 Hz, 1H), 6.75-6.81 (m, 1H), 6.87 (s, 1H), 7.72 (d, J=8.2 Hz, 1H)

Intermediate 9

2-Isopropoxy-4-chloro-1-nitro-benzene

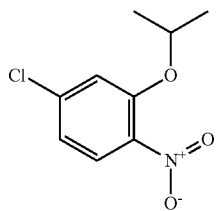

Intermediate 9 was prepared analogously to Intermediate 7 with 2-fluoro-4-chloro-nitrobenzene to give 2-isopropoxy-4-chloro-1-nitro-benzene; 99% yield; $^1$H NMR (400 MHz, CHLOROFORM-d) δ ppm 1.41 (d, J=6.0 Hz, 6H), 4.66 (apt, J=6.0 Hz, 1H), 6.93-7.00 (m, 1H), 7.03-7.09 (m, 1H), 7.72-7.81 (m, 1H)

Intermediate 10

2-Isopropoxy-4-methoxy-1-nitro-benzene

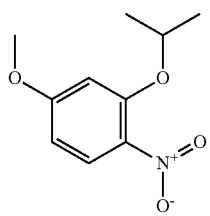

Intermediate 10 was prepared analogously to Intermediate 7 with 2-fluoro-4-methoxy-nitrobenzene to give 2-isopropoxy-4-methoxy-1-nitro-benzene; 98% yield; $^1$H NMR (400 MHz, CHLOROFORM-d) δ ppm 1.41 (d, J=6.0 Hz, 6H), 3.82-3.94 (s, 3H), 4.64 (spt, J=6.0 Hz, 1H), 6.49 (dd, J=8.9, 2.5 Hz, 1H), 6.53 (m, J=2.7 Hz, 1H), 7.94 (d, J=8.9 Hz, 1H)

Intermediate 11

3-Isopropoxy-4-aminobenzonitrile

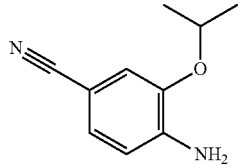

A solution of Intermediate 7 (200 mg, 0.97 mmol) in 50:50 EtOAc:MeOH (25 ml) was passed through the H-Cube (Cartridge: 10% Pd/C cartridge; flow rate: 1 ml/min; temperature: 30° C.; pressure: Full H$_2$ pressure) The final solution was concentrated to give a light yellow oil (151 mg, 88%); $^1$H NMR (400 MHz, CHLOROFORM-d) δ ppm 1.34 (d, J=5.95 Hz, 6H), 4.31 (br. s., 2H), 4.51 (spt, J=6.03 Hz, 1H), 6.62-6.66 (m, 1H), 6.92-6.95 (m, 1H), 7.02-7.08 (m, 1H).

Intermediate 12

2-lsopropoxy-4-methylaniline

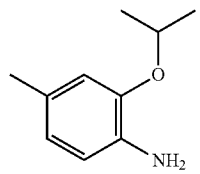

Intermediate 12 was prepared analogously to Intermediate 11 from Intermediate 8 to give 2-isopropoxy-4-methylaniline; $^1$H NMR (400 MHz, CHLOROFORM-d) δ ppm 1.34 (d, J=6.0 Hz, 6H), 2.24 (s, 3H), 3.61 (br. s., 2H), 4.50 (spt, J=6.0 Hz, 1H), 6.56-6.59 (m, 1H), 6.61-6.64 (m, 2H)

Intermediate 13

2-Isopropoxy-4-methoxyaniline

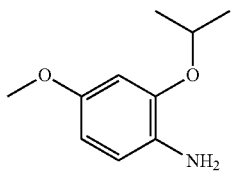

Intermediate 13 was prepared analogously to Intermediate 11 with Intermediate 10 to give 2-isopropoxy-4-methoxyaniline; $^1$H NMR (400 MHz, CHLOROFORM-d) δ ppm 1.35 (d, J=6.0 Hz, 6H), 3.73 (s, 3H), 4.49 (spt, J=6.0 Hz, 1H), 6.31-6.37 (m, 1H), 6.42-6.47 (m, 1H), 6.62-6.68 (m, 1H)

Intermediate 14

4-Chloro-2-isopropoxy-aniline

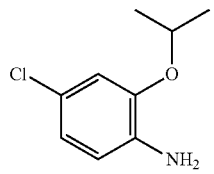

To a solution of Intermediate 9 (200 mg, 0.93 mmol) and acetic acid (5 ml) in EtOH (30 ml) was added iron powder and stirred for 2 hours. The compound was concentrated, the reside taken up in MeOH and passed through a SCX cartridge, the product eluting with 2M $NH_3$ in MeOH to give 4-chloro-2-isopropoxy-aniline, which was used in the next step without further purification.

Intermediate 15

(1R,2R)-2-(5-fluoro-2-nitro-fluoro

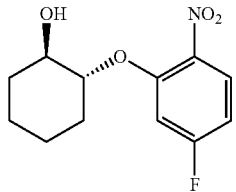 [SMILES: O=[N+]([O-])c1ccc(F)cc1O[C@@H]1CCCC[C@H]1O]

LiHMDS (8.6 ml, 8.6 mmol, 1M in THF) was added slowly to 1,2-Cyclohexanediol, (1R, 2R)-(1 g, 8.6 mmol) in THF (10 ml) at room temperature. An additional (5 ml) of THF was added and the mixture was stirred for 5 minutes, then 2,4-difluoro-1-nitro-benzene (0.943 ml, 8.6 mmol) was added dropwise. The mixture stirred at room temperature overnight. The mixture was diluted with EtOAc and 2M HCl (aq), the organic layer separated and washed with 2M NaOH (aq), then eluted through a phase separator and concentrated. Purification by column chromatography, eluting with 0-15% EtOAc/petroleum ether gave a yellow solid (1.2 g, 55%); $^1$H NMR (400 MHz, DMSO-$d_6$) δ ppm 0.97-1.44 (m, 4H), 1.48-1.65 (m, 2H), 1.69-1.85 (m, 1H), 1.87-2.10 (m, 1H), 3.41-3.68 (m, 1H), 4.12-4.41 (m, 1H), 4.92 (br. s, 1H), 6.76-7.02 (m, 1H), 7.39 (dd, J=11.45, 2.75 Hz, 1H), 7.91 (dd, J=9.16, 6.41 Hz, 1H).

Intermediate 16

(1R,2R)-2-(2-amino-5-fluoro-phenoxy)cyclohexanol

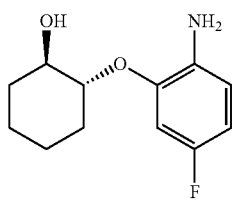 [SMILES: Nc1ccc(F)cc1O[C@@H]1CCCC[C@H]1O]

A solution of Intermediate 15 (1.2 g, 4.7 mmol) in 5:1 EtOH:EtOAc (120 ml) was passed through the H-Cube reactor (Cartridge: 10% Pd/C, flow rate: 1 ml/min; temperature: room temperature; pressure: 1 bar). The solution was concentrated to give a brown gum (1.05 mg, 99%); $^1$H NMR (400 MHz, DMSO-$d_6$) δ ppm 1.16-1.37 (m, 4H), 1.51-1.64 (m, 2H), 1.78-1.88 (m, 1H), 1.95 (s, 1H), 3.44-3.56 (m, 1H), 3.69-3.81 (m, 1H), 4.66 (br. s., 2H), 5.04 (d, J=4.58 Hz, 1H), 6.47 (m, 1H), 6.50-6.58 (m, 1H), 6.65-6.73 (m, 1H); LC-MS (ESI): (MH$^+$) 226.1

Intermediate 17

4-Fluoro-2-[(1R,2R)-2-methoxycyclohexoxy]-1-nitro-benzene

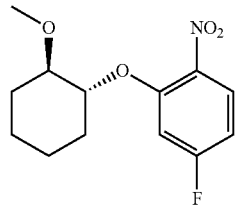

Intermediate 15 (1.36 g, 5.33 mmol) and trimethyloxonium tetrafluoroborate (2.36 g, 16 mmol) were combined in DCM (30 ml) and stirred at room temperature overnight. The mixture was diluted with water, the organic layer separated, dried over MgSO$_4$ and concentrated. Purification by column chromatography, eluting. with 2-5% EtOAc/petroleum ether gave a yellow oil (1 g, 70%); $^1$H NMR (400 MHz, CHLOROFORM-d) δ ppm 1.16-1.43 (m, 3H), 1.50-1.65 (m, 1H), 1.66-1.85 (m, 2H), 2.01-2.21 (m, 2H), 3.29-3.41 (m, 4H), 4.14-4.27 (m, 1H), 6.62-6.72 (m, 1H), 6.87-6.94 (m, 1H), 7.82-7.91 (m, 1H)

Intermediate 18

4-Fluoro-2-[(1R,2R)-2-methoxycyclohexoxy]aniline

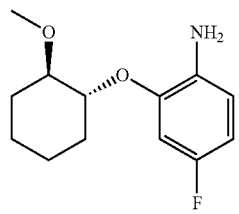 [SMILES: CO[C@@H]1CCCC[C@H]1Oc1cc(F)ccc1N]

Intermediate 18 was prepared analogously to intermediate 16 to give 4-fluoro-2-[(1R,2R)-2-methoxycyclohexoxy]aniline as a golden oil (0.84 g, 95%); $^1$R NMR (400 MHz, CHLOROFORM-d) δ ppm 1.18-1.39 (m, 3H), 1.42-1.56 (m, 1H), 1.63-1.79 (m, 2H), 2.05-2.18 (m, 2H), 3.28-3.38 (m, 1H), 3.44 (s, 3H), 3.94 (m, 1H), 6.49-6.58 (m, 1H), 6.63-6.72 (m, 2H); (MH$^+$) 240.2.

Intermediate 19

(1S,2S)-2-(5-Fluoro-2-nitro-phenoxy)cyclohexanol

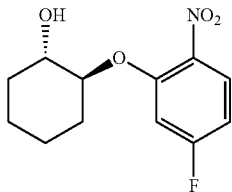 [SMILES: O=[N+]([O-])c1ccc(F)cc1O[C@H]1CCCC[C@@H]1O]

Intermediate 19 was prepared analogously to Intermediate 15 to give a yellow solid (1.9 g, 29%); $^1$H NMR (400 MHz, DMSO-$d_6$) δ ppm 1.14-1.41 (m, 4H), 1.51-1.63 (m, 2H), 1.75-1.85 (m, 1H), 1.90-2.01 (m, 1H), 3.44-3.53 (m, 1H), 4.26-4.35 (m, 1H), 4.94 (d, J=5.04 Hz, 1H), 6.84-6.92 (m, 1H), 7.39 (dd, J=11.45, 2.29 Hz, 1H), 7.91 (dd, J=9.16, 5.95 Hz, 1H)

Intermediate 20

(1S,2S)-2-(2-amino-5-fluoro-phenoxy)cyclohexanol

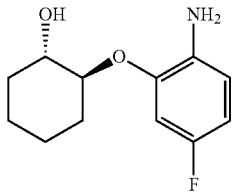 [SMILES: Nc1ccc(F)cc1O[C@H]1CCCC[C@@H]1O]

Prepared analogously to Intermediate 16 to give a brown gum (0.95 g), which was used in the next step without further purification. $^1$H NMR (400 MHz, DMSO-$d_6$) δ ppm 1.16-1.33 (m, 4H), 1.48-1.66 (m, 2H), 1.78-1.87 (m, 1H), 1.93-2.04 (m, 1H), 3.45-3.54 (m, 1H), 3.71-3.80 (m, 1H), 4.63 (s, 2H), 5.04 (d, J=4.58 Hz, 1H), 6.42-6.49 (m, 1H), 6.50-6.57 (m, 1H), 6.65-6.72 (m, 1H); (MH$^+$) 226

Intermediate 21

4-fluoro-2-[(1S,2S)-2-methoxycyclohexoxy]-1-nitrobenzene

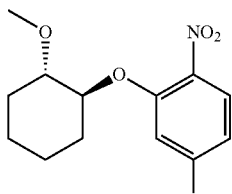

Intermediate 21 was prepared analogously to Intermediate 17 to give a yellow oil (0.63 g, 66%); $^1$H NMR (400 MHz, CHLOROFORM-d) δ ppm 1.22-1.41 (m, 3H), 1.55 (m, 1H), 1.66-1.81 (m, 2H), 2.02-2.18 (m, 2H), 3.29-3.41 (m, 4H), 4.13-4.25 (m, 1H), 6.62-6.72 (m, 1H), 6.91 (dd, J=10.53, 2.75 Hz, 1H), 7.82-7.91 (m, 1H)

Intermediate 22

4-Fluoro-2-[(1S,2S)-2-methoxycyclohexoxy]aniline

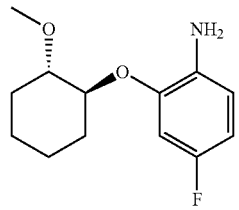 [SMILES: CO[C@H]1CCCC[C@@H]1Oc1cc(F)ccc1N]

Intermediate 22 was prepared analogously to Intermediate 16 to give 4-fluoro-2-[(1S,2S)-2-methoxycyclohexoxy]aniline as a brown oil (0.54 g, 97%); 1H NMR (400 MHz, CHLOROFORM-d) δ ppm 1.21-1.39 (m, 3H), 1.42-1.54 (m, 1H), 1.63-1.81 (m, 2H), 2.03-2.17 (m, 2H), 3.28-3.36 (m, 1H), 3.44 (s, 3H), 3.88-3.99 (m, 1H), 6.50-6.58 (m, 1H), 6.65-6.72 (m, 2H); (MH+) 240.2

Intermediate 23

4-(Methylsulfanyl)-5H-pyrrolo[3,2-d]pyrimidine

A mixture of 4-chloro-5H-pyrrolo[3,2-d]pyrimidine (5.0 g, 32.5 mmol) and sodium thiomethoxide (6.8 g, 97.4 mmol) in DMF (75 ml) was stirred at rt for 3 hours. The mixture was diluted with EtOAc and water and the organic phase was washed with water (×3) and brine (×1). The original aqueous phase was re-extracted with DCM. The DCM layer was washed with water (×2). The EtOAc and DCM extracts were combined, dried and concentrated. The crude product was pre-absorbed onto silica gel and purified by flash chromatography on silica gel eluting with 3:1 EtOAc:petroleum ether then EtOAc and finally with 5% MeOH in EtOAc to give a pale yellow solid 2.97 g (55%). $^1$H NMR (400 MHz, DMSO-$d_6$) δ ppm 2.67 (s, 3H), 6.53-6.62 (m, 1H), 7.67-7.79 (m, 1H), 8.64 (s, 1H), 12.03 (br.s., 1H).

Intermediate 24

5-[(4-Methylphenyl)sulfonyl]-4-(methylsulfanyl)-5H-pyrrolo[2,3-d]pyrimidine

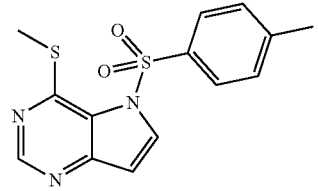 [SMILES: CSc1ncnc2ccn(S(=O)(=O)c3ccc(C)cc3)c12]

Intermediate 25

Ethyl 5-[(4-methylphenyl)sulfonyl]-4-(methylsulfanyl)-5H-pyrrolo[3,2-d]pyrimidine-6-carboxylate

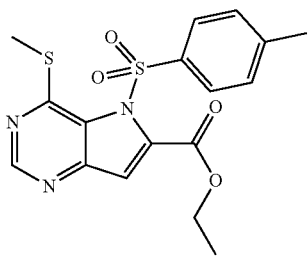 [SMILES: CCOC(=O)c1cc2ncnc(SC)c2n1S(=O)(=O)c1ccc(C)cc1]

n-Butyllithium, 1.6M in hexanes (14.7 ml, 23.6 mmol) was added dropwise to a solution of Intermediate 24 (4.42 g, 13.9 mmol) in THF (250 ml) at −78° C. The reaction was allowed to stir at −78° C. for 1.75 h. Ethyl chloroformate (2.93 ml, 30.5 mmol) was then added dropwise and the reaction mixture was stirred at −78° C. for one hour and then allowed to warm to 0° C. The mixture was stirred at 0° C. for 30 minutes and then quenched with sat. NH$_4$Cl (aq). The mixture was extracted with EtOAc (×2) and the combined organic extracts were washed with brine, dried and concentrated. The crude product was purified by flash chromatography on silica gel in 2:1 petroleum ether:EtOAc to give an orange solid 2.87 g (53%). $^1$H NMR (400 MHz, DMSO-d$_6$) δ ppm 1.24 (t, J=7.33 Hz, 3H), 2.40 (s, 3H), 2.55 (s, 3H), 4.33 (q, J=6.87 Hz, 2H), 7.48 (d, J=8.24 Hz, 2H), 7.57 (s, 1H), 7.96 (m, 2H), 8.90 (s, 1H).

Intermediate 26

Ethyl 4-(methylsulfanyl)-5H-pyrrolo[3,2-d]pyrimidine-6-carboxylate

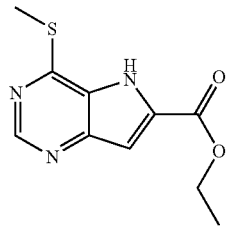 [SMILES: CCOC(=O)c1cc2ncnc(SC)c2[nH]1]

A solution of sodium ethoxide in ethanol (21% w/v, 4.74 ml) was added to an ice-cooled solution of Intermediate 25 (2.87 g, 7.34 mmol) in ethanol (80 ml), and the mixture was stirred 0° C. for 2 hours. 1M HCl was then added to adjust the pH to 6 and the mixture was concentrated to dryness. The crude product was pre-absorbed on to silica gel prior to purification by flash chromatography on silica gel eluting with 2:1 EtOAc:petroleum ether followed by a gradient of 2% to 50% MeOH in EtOAc to provide a pale brown solid (1.43 g, 82%). $^1$H NMR (400 MHz, DMSO-d$_6$) δ ppm 1.36 (t, J=7.10 Hz, 3H), 2.66 (s, 3H), 4.39 (q, J=7.33 Hz, 2H), 7.16-7.20 (m, 1H), 8.73 (s, 1H).

Intermediate 27

Ethyl 5-methyl-4-(methylsulfanyl)-5H-pyrrolo[3,2-d]pyrimidine-6-carboxylate

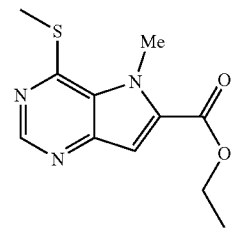

A mixture of Intermediate 26 (1.03 g, 4.35 mmol), caesium carbonate (3.07 g, 8.69 mmol) and iodomethane (271 μl, 4.35 mmol) in DMF (40 ml) was stirred at rt for 4 hours. The reaction mixture was diluted with water and extracted with EtOAc (×2). The combined organic extracts were washed with water (×3), brine (×1), dried and concentrated. The crude product was pre-absorbed on to silica gel prior to purification by flash chromatography on silica gel eluting with 2:1 petroleum ether:EtOAc to give a pale pink coloured solid (574 mg, 53%) $^1$H NMR (400 MHz, DMSO-d$_6$) δ ppm 1.35 (t, J=7.10 Hz, 3H), 2.69 (s, 3H), 4.32-4.41 (m, 5H), 7.22 (s, 1H), 8.71 (s, 1H).

Intermediate 28

Ethyl 4,7-dichloro-5-methyl-5H-pyrrolo[3,2-d]pyrimidine-6-carboxylate

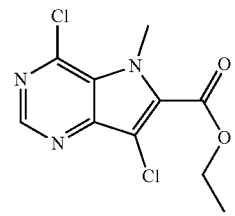

A solution of sulfuryl chloride (756 μl, 9.32 mmol) in DCM (30 ml) was added, dropwise, to an ice-cooled solution of Intermediate 27 (468 mg, 1.86 mmol) in acetonitrile (30 ml). The reaction was stirred at 0° C. for 1.5 hours. Sat. NaHCO$_3$ (aq) was added to adjust the pH to above 7. The aqueous phase was re-extracted with DCM. The combined organic phases were washed with water, dried and concentrated. The crude product was pre-absorbed onto silica gel prior to purification by flash chromatography on silica gel eluting with 3:1 petroleum ether:EtOAc to give a pale yellow solid (409 mg, 80%). $^1$H NMR (400 MHz, DMSO-d$_6$) δ ppm 1.39 (t, J=7.10 Hz, 3H), 4.26 (s, 3H), 4.47 (q, J=7.33 Hz, 2H), 8.81 (s, 1H).

Intermediate 29

Ethyl 7-chloro-4-{[4-fluoro-2-(propan-2-yloxy)phenyl]amino}-5-methyl-5H-pyrrolo[3,2-d]pyrimidine-6-carboxylate

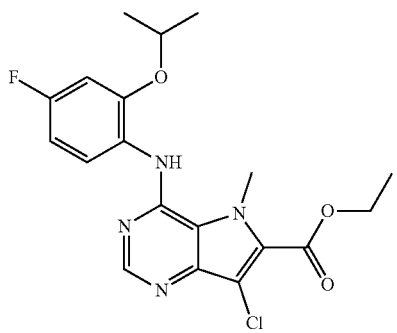 [SMILES: CCOC(=O)c1c(Cl)c2ncnc(Nc3ccc(F)cc3OC(C)C)c2n1C]

A mixture of Intermediate 28 (320 mg, 1.17 mmol), 4-fluoro-2-isopropoxyaniline (179 µl, 1.17 mmol) and PTSA (22 mg, 0.117 mmol) in IPA (15 ml) was stirred and heated at 60° C. for 3 hours. The reaction was allowed to cool to rt and then concentrated to dryness. The residue was diluted with DCM and washed with sat. NaHCO$_3$ (aq). The aqueous phase was re-extracted with DCM. The combined organic phases were dried and concentrated. The crude product was pre-absorbed on to silica gel prior to purification by flash chromatography on silica gel eluting with 40:1 DCM:IPA to give a pale beige coloured solid (395 mg, 83%). $^1$H NMR (400 MHz, DMSO-d$_6$) δ ppm 1.27 (d, J=5.95 Hz, 6H), 1.38 (t, J=7.10 Hz, 3H), 4.31 (s, 3H), 4.37-4.47 (m, 2H), 4.73 (dt, J=12.02, 6.13 Hz, 1H), 6.77-6.86 (m, 1H), 7.07 (dd, J=10.99, 2.75 Hz, 1H), 8.27 (dd, J=8.70, 6.41 Hz, 1H), 8.38 (s, 1H), 8.43 (s, 1H)

Intermediate 30

Ethyl 4-{[4-fluoro-2-(propan-2-yloxy)phenyl]amino}-5-methyl-5H-pyrrolo[3,2-d]pyrimidine-6-carboxylate

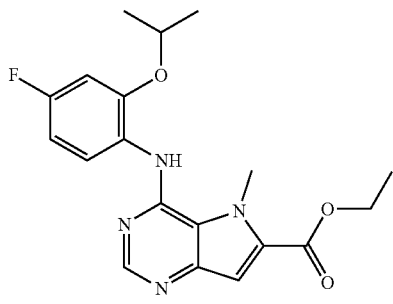 [SMILES: CCOC(=O)c1cc2ncnc(Nc3ccc(F)cc3OC(C)C)c2n1C]

Intermediate 29 (230 mg, 0.565 mmol), ammonium formate (712 mg, 11.3 mmol) and 10% palladium on charcoal (116 mg) in EtOAc (25 ml) were stirred and heated under reflux for 1 hour. The reaction mixture was cooled to rt and filtered through Celite. The filtrate was diluted with EtOAc and washed with water and brine, and the organic phase was dried and concentrated. The crude product was purified by flash chromatography on silica gel eluting with 40:1 DCM: IPA to give a pale brown solid (155 mg, 74%). $^1$H NMR (400 MHz, DMSO-d$_6$) δ ppm 1.26-1.38 (m, 9H), 4.36 (q, J=7.33 Hz, 2H), 4.44 (s, 3H), 4.75 (quin, J=6.07 Hz, 1H), 6.81 (td, J=8.70, 2.75 Hz, 1H), 7.07 (dd, J=10.99, 2.75 Hz, 1H), 7.12 (s, 1H), 8.30-8.42 (m, 3H).

Intermediate 31

4-{[4-fluoro-2-(propan-2-yloxy)phenyl]amino}-5-methyl-5H-pyrrolo[3,2-d]pyrimidine-6-carboxylic acid

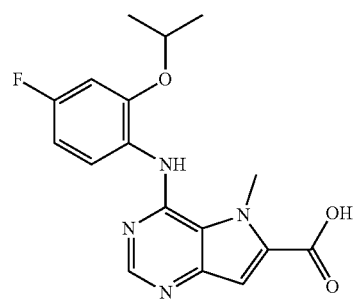 [SMILES: CC(C)Oc1cc(F)ccc1Nc1ncnc2cc(C(=O)O)n(C)c12]

A mixture of Intermediate 30 (155 mg, 0.417 mmol) and 1 N NaOH (1.25 ml, 1.25 mmol) in 1:1 THF:MeOH (12 ml) was stirred at rt for 2 hours. The reaction was cooled in an ice-bath and 1 M HCl was added to pH=4/5. The mixture was then concentrated to dryness. The solid residue was dispersed in to water and the mixture was filtered to give a pale beige coloured solid 127 mg (89%). $^1$H NMR (400 MHz, DMSO-d$_6$) δ ppm 1.29 (d, J=5.95 Hz, 6H), 4.47 (s, 3H), 4.75 (dt, J=11.91, 5.95 Hz, 1H), 6.81 (td, J=8.70, 2.75 Hz, 1H), 7.03-7.11 (m, 2H), 8.26-8.48 (m, 3H).

Intermediate 32

Tert-butyl 4-({[(4-{[4-fluoro-2-(propan-2-yloxy)phenyl]amino}-5-methyl-5H-pyrrolo[3,2-d]pyrimidin-6-yl)carbonyl]amino}methyl)piperidine-1-carboxylate

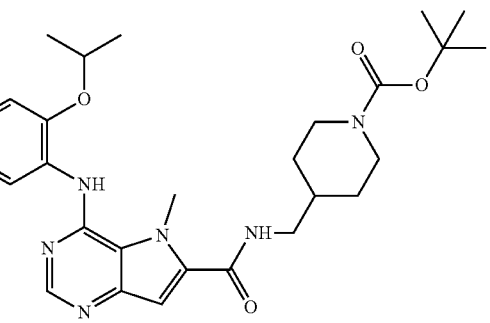

A mixture of Intermediate 31 (75 mg, 0.218 mmol), 1-Boc-4-(aminomethyl)piperidine (47 mg, 0.218 mmol) and DIPEA (190 µl, 1.09 mmol) in DMF (5 ml) was stirred at rt for 10 minutes. HATU (116 mg, 0.305 mmol) was then added, and the reaction mixture was stirred at rt overnight. The mixture was then diluted with water and extracted with EtOAc, the organic phase was washed with water (×3) and brine (×1), dried and concentrated. The crude product was purified by flash chromatography on silica gel eluting with 40:1 to 20:1 DCM:2 M NH$_3$ in MeOH to give an off-white solid 82 mg (70%). $^1$H NMR (400 MHz, DMSO-d$_6$) δ ppm 0.96-1.12 (m, 2H), 1.29 (d, J=5.95 Hz 6H), 1.39 (s, 9H), 1.63-1.80 (m, 3H), 2.57-2.80 (m, 2H), 3.17 (t, J=6.18 Hz, 2H), 3.88-4.00 (m, 2H), 4.37 (s, 3H), 4.68-4.82 (m, 1H), 6.80 (td, J=8.82, 2.98 Hz, 1H), 6.96 (s, 1H), 7.06 (dd, J=10.99, 2.75 Hz, 1H), 8.23 (s, 1H), 8.33 (s, 1H), 8.44 (dd, J=9.16, 6.41 Hz, 1H), 8.75 (t, J=5.72 Hz, 1H). m/z (ES+APCI)$^+$: 541 [M+H]$^+$ Intermediate 33 tert-Butyl 4-(2-{[(4-{[4-fluoro-2-(propan-2-yloxy)phenyl]amino}-5-methyl-5H-pyrrolo[3,2-d]pyrimidin-6-yl)carbonyl]amino}ethyl)piperazine-1-carboxylate

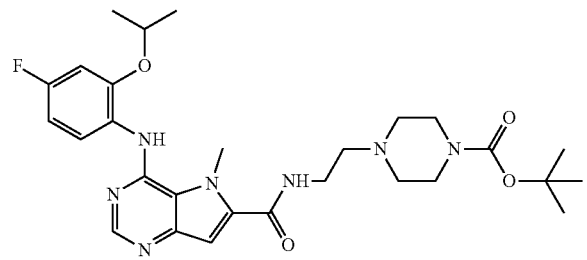 [SMILES: CC(C)Oc1cc(F)ccc1Nc1ncnc2cc(C(=O)NCCN3CCN(C(=O)OC(C)(C)C)CC3)n(C)c12]

Intermediate 33 was prepared in analogous fashion to Intermediate 32 to provide a pale brown coloured solid (yield 48%). $^1$H NMR (400 MHz, DMSO-d$_6$) δ ppm 1.29 (d, J=5.95 Hz, 6H), 1.39 (s, 9H), 2.36-2.44 (m, 4H), 3.19-3.47 (m, 8H), 4.38 (s, 3H), 4.75 (dt, J=12.25, 6.01 Hz, 1H), 6.80 (td, J=8.70, 2.75 Hz, 1H), 6.92 (s, 1H), 7.06 (dd, J=10.99, 2.75 Hz, 1H), 8.23 (s, 1H), 8.32 (s, 1H), 8.44 (dd, J=9.16, 6.41 Hz, 1H), 8.66 (t, J=5.72 Hz, 1H). m/z (ES+APCI)$^+$: 556 [M+H]$^+$ Intermediate 34

7-Chloro-4-{[4-fluoro-2-(propan-2-yloxy)phenyl]amino}-5-methyl-5H-pyrrolo[3,2-d]pyrimidine-6-carboxylic acid

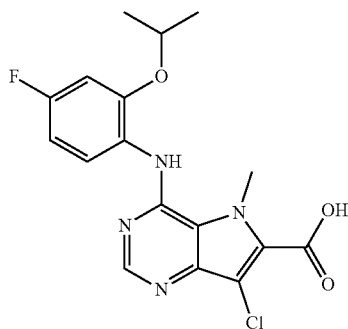 [SMILES: CC(C)Oc1cc(F)ccc1Nc1ncnc2c(Cl)c(C(=O)O)n(C)c12]

Intermediate 34 was prepared in analogous fashion to Intermediate 31 to provide a white solid (yield 93%). $^1$H NMR (400 MHz, DMSO-d$_6$) δ ppm 1.27 (d, J=5.95 Hz, 6H), 4.34 (s, 3H), 4.73 (dt, J=11.91, 5.95 Hz, 1H), 6.81 (td, J=8.70, 2.75 Hz, 1H), 7.07 (dd, J=10.76, 2.52 Hz, 1H), 8.21-8.49 (m, 3H). m/z (ES+APCI)$^+$: 379/381 [M+H]$^+$ Example 1

5-Ethyl-N-(4-fluoro-2-isopropoxy-phenyl)pyrrolo[3,2-d]pyrimidin-4-amine

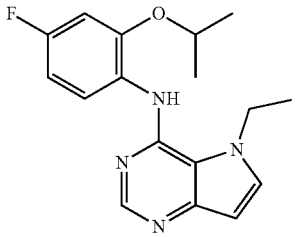

2-Isopropoxy-4-fluoroaniline (55 mg, 0.33 mmol), Intermediate 2 (54 mg, 0.30 mmol), 4M HCl in dioxane (0.1 ml) and IPA (2 ml) were heated in the microwave at 140° C. for 20 min. The mixture was concentrated and purified by preparative LCMS to give a white solid (41 mg, 44%); $^1$H NMR (400 MHz, CHLOROFORM-d) δ ppm 1.43 (d, J=6.0 Hz, 6H), 1.61 (t, J=7.3 Hz, 3H), 4.45 (q, J=7.3 Hz, 2H), 4.68 (spt, J=6.0 Hz, 1H), 6.60 (d, J=3.2 Hz, 1H), 6.69 (dd, J=10.0, 2.7 Hz, 1H), 6.75 (td, J=8.7, 2.7 Hz, 1H), 7.24 (d, J=3.2 Hz, 1H), 7.58 (br. s, 1H), 8.54 (s, 1H), 8.75 (dd, J=8.9, 6.2 Hz, 1H); LC-MS (ESI): (MH$^+$) 315.2

Example 2

N-(4-fluoro-2-isopropoxy-phenyl)-5-propyl-pyrrolo[3,2-d]pyrimidin-4-amine

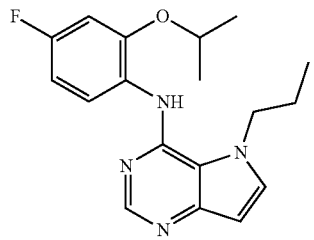 [SMILES: CCCn1ccc2ncnc(Nc3ccc(F)cc3OC(C)C)c21]

Example 2 was prepared analogously to Example 1 with Intermediate 3 and 2-isopropoxy-4-fluoroaniline to give N-(4-fluoro-2-isopropoxy-phenyl)-5-propyl-pyrrolo[3,2-d]pyrimidin-4-amine (5%); $^1$H NMR (400 MHz, CHLOROFORM-d) δ ppm 0.99 (t, J=7.3 Hz, 3H), 1.43 (d, J=5.9 Hz, 6H), 2.01 (sxt, J=7.1 Hz, 2H), 4.42 (t, J=6.9 Hz, 2H), 4.70 (spt, J=6.0 Hz, 1H), 6.69-6.80 (m, 2H), 6.88 (d, J=3.2 Hz, 1H), 7.40 (d, J=3.2 Hz, 1H), 8.13 (br. s, 1H), 8.51-8.58 (m, 1H), 8.66 (s, 1H); LC-MS (ESI): (MH$^+$) 329.2

Example 3

N-(4-fluoro-2-isopropoxy-phenyl)-5-isopropyl-pyrrolo[3,2-d]pyrimidin-4-amine

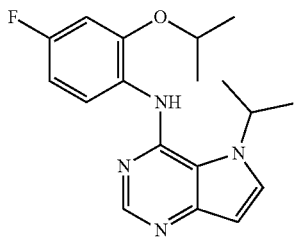 [SMILES: CC(C)Oc1cc(F)ccc1Nc1ncnc2ccn(C(C)C)c12]

Example 3 was prepared analogously to Example 1 with Intermediate 4 and 2-isopropoxy-4-fluoroaniline to give the product (10%); $^1$H NMR (400 MHz, CHLOROFORM-d) δ ppm 1.40-1.45 (d, J=6.0 Hz, 6H), 1.68 (d, J=6.9 Hz, 6H), 4.68 (spt, J=6.0 Hz, 1H), 4.96 (spt, J=6.9 Hz, 1H), 6.65 (d, J=3.2 Hz, 1H), 6.70 (dd, J=10.0, 2.7 Hz, 1H), 6.75 (td, J=8.7, 2.7 Hz, 1H), 7.45 (d, J=3.2 Hz, 1H), 7.61 (br. s, 1H), 8.55 (s, 1H), 8.65-8.73 (m, 1H); LC-MS (ESI): (MH$^+$) 329.2

Example 4

2-[4-(4-Fluoro-2-isopropoxy-anilino)pyrrolo[3,2-d]pyrimidin-5-yl]ethanol

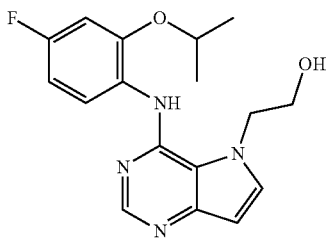 [SMILES: CC(C)Oc1cc(F)ccc1Nc1ncnc2ccn(CCO)c12]

Example 4 was prepared analogously to Example 1 with Intermediate 5 and 2-isopropoxy-4-fluoroaniline to give 2-[4-(4-fluoro-2-isopropoxy-anilino)pyrrolo[3,2-d]pyrimidin-5-yl]ethanol (7%); $^1$H NMR (400 MHz, CHLOROFORM-d) δ ppm 1.47 (d, J=6.0 Hz, 6H), 4.09 (t, J=4.8 Hz, 2H), 4.38 (t, J=4.6 Hz, 2H), 4.67 (spt, J=6.0 Hz, 1H), 6.07 (d, J=3.2 Hz, 1H), 6.13 (br. s., 1H), 6.62-6.76 (m, 2H), 6.90 (d, J=3.2 Hz, 1H), 8.16 (dd, J=8.7, 6.4 Hz, 1H), 8.20 (s, 1H), 8.58 (br. s, 1H); LC-MS (ESI): (MH$^+$) 331.2

Example 5

N-(4-fluoro-2-isopropoxy-phenyl)-5-(2-methoxyethyl)pyrrolo[3,2-d]pyrimidin-4-amine

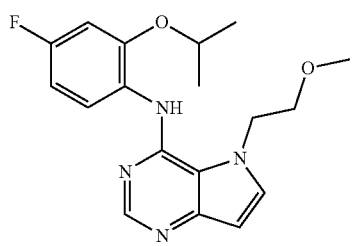 [SMILES: COCCn1ccc2ncnc(Nc3ccc(F)cc3OC(C)C)c21]

Example 5 was prepared analogously to Example 1 with Intermediate 6 and 2-isopropoxy-4-fluoroaniline to give the desired product (56 mg, 46%); $^1$H NMR (400 MHz, CHLOROFORM-d) δ ppm 1.40 (d, J=6.41 Hz, 6H), 3.34 (s, 3H), 3.79 (t, J=5.00 Hz, 2H), 4.55 (t, J=5.04 Hz, 2H), 4.62 (spt, J=6.03 Hz, 1H), 6.61 (d, J=3.21 Hz, 1H), 6.65-6.74 (m, 2H), 7.22 (d, J=3.20 Hz, 1H), 8.15 (br. s, 1H), 8.40-8.48 (m, 1H), 8.51 (s, 1H); LC-MS (ESI): (MH$^+$) 345.2

Example 6

N-(6-chloro-2-isopropoxy-3-pyridyl)-5-methyl-pyrrolo[3,2-d]pyrimidin-4-amine

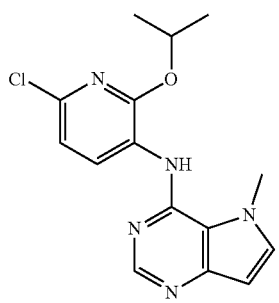

Step 1 (6-chloro-2-isopropoxy-3-amino-pyridine)

To a solution of 2-propanol (344 mg, 5.7 mmol) in toluene at 0° C., was added a sodium hydride as a 60% dispersion in mineral oil (250 mg, 6.25 mmol) and the mixture stirred for 45 min. 2,6-Dichloro-3-nitropyridine was then added and stirring was continued overnight. The mixture was concentrated, the residue taken up in EtOAc, washed with water, dried and concentrated to give 6-chloro-2-isopropoxy-3-nitro-pyridine, a yellow solid. The yellow solid was taken up in acetic acid (0.3 ml) and ethanol (10 ml) and iron powder (520 mg, 9.26 mmol) was then added and the mixture stirred for 3 hours. The mixture was filtered through a plug of celite and then a plug of silica. The filtrate was washed with sat. NaHCO$_{3(aq)}$, the organic layer separated, dried and concentrated to give 6-chloro-2-isopropoxy-3-amino-pyridine, which was used in the next step without further purification.

Step 2

Intermediate 1 (50 mg, 0.3 mmol), 6-chloro-2-isopropoxy-3-amino-pyridine (67 mg, 0.36 mmol), 4M HCl in dioxane (0.1 ml) and IPA (2 ml) were heated in the microwave at 140° C. for 20 minutes. The mixture was concentrated and submitted for HPLC purification. To give N-(6-chloro-2-isopropoxy-3-pyridyl)-5-methyl-pyrrolo[3,2-d]pyrimidin-4-amine, a white solid (22 mg, 23%); $^1$H NMR (400 MHz, CHLOROFORM-d) δ ppm 1.43 (d, J=6.20 Hz, 6H), 4.20 (s, 3H), 5.45 (spt, J=6.18 Hz, 1H), 6.56 (d, J=3.20 Hz, 1H), 6.96 (d, J=8.20 Hz, 1H), 7.17 (d, J=3.20 Hz, 1H), 7.70 (br. s, 1H), 8.53 (s, 1H), 9.04 (d, J=8.20 Hz, 1H); LC-MS (ESI): (MH$^+$) 318/320.

Example 7

3-Isopropoxy-4-[(5-methylpyrrolo[3,2-d]pyrimidin-4-yl)amino]benzonitrile

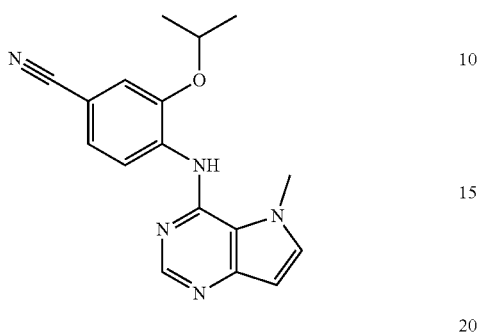

Intermediate 11 (63 mg, 0.36 mmol), Intermediate 1 (50 mg, 0.30 mmol), 4 m HCl in dioxane (0.1 ml) and IPA (2 ml) were heated in the microwave at 140° C. for 20 min. The mixture was concentrated and purified by preparative LCMS to give a white solid (10.5 mg, 11%); $^1$H NMR (400 MHz, CHLOROFORM-d) δ ppm 1.46 (d, J=6.00 Hz, 6H), 4.21 (s, 3H), 4.74 (spt, J=6.03 Hz, 1H), 6.59 (d, J=3.21 Hz, 1H), 7.13 (d, J=1.37 Hz, 1H), 7.20 (d, J=3.21 Hz, 1H), 7.36 (dd, J=8.24, 1.83 Hz, 1H), 8.15 (s, 1H), 8.59 (s, 1H), 8.96-9.05 (m, 1H); LC-MS (ESI): (MH$^+$) 308.

Example 8

N-(2-isopropoxy-4-methyl-phenyl)-5-methyl-pyrrolo[3,2-d]pyrimidin-4-amine

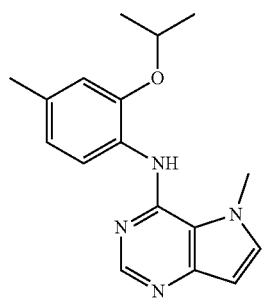 [SMILES: Cc1ccc(Nc2ncnc3ccn(C)c23)c(OC(C)C)c1]

Example 8 was prepared analogously to Example 7 with Intermediate 1 and Intermediate 12 to give N-(2-isopropoxy-4-methyl-phenyl)-5-methyl-pyrrolo[3,2-d]pyrimidin-4-amine (22% yield); $^1$H NMR (400 MHz, CHLOROFORM-d) δ ppm 1.40 (d, J=6.0 Hz, 6H), 2.35 (s, 3H), 4.20 (s, 3H), 4.69 (spt, J=6.0 Hz, 1H), 6.53 (d, J=2.7 Hz, 1H), 6.75 (d, J=1.8 Hz, 1H), 6.84 (dd, J=8.2, 0.9 Hz, 1H), 7.11 (d, J=3.2 Hz, 1H), 7.83 (br. s, 1H), 8.50 (s, 1H), 8.61 (d, J=8.2 Hz, 1H); LC-MS (ESI): (MH$^+$) 297.0

Example 9

N-(4-chloro-2-isopropoxy-phenyl)-5-methyl-pyrrolo[3,2-d]pyrimidin-4-amine

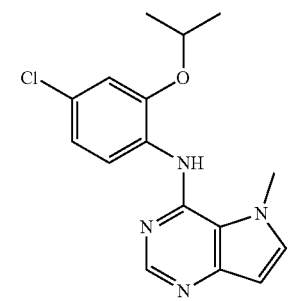 [SMILES: CC(C)Oc1cc(Cl)ccc1Nc1ncnc2ccn(C)c12]

Example 9 was prepared analogously to Example 7 with Intermediate 1 and Intermediate 14 to give N-(4-chloro-2-isopropoxy-phenyl)-5-methyl-pyrrolo[3,2-d]pyrimidin-4-amine (26% yield); $^1$H NMR (400 MHz, CHLOROFORM-d) δ ppm 1.42 (d, J=6.0 Hz, 6H), 4.22 (s, 3H), 4.68 (spt, J=6.0 Hz, 1H), 6.55 (d, J=3.2 Hz, 1H), 6.90 (d, J=2.3 Hz, 1H), 7.01 (dd, J=8.7, 2.3 Hz, 1H), 7.14 (d, J=2.7 Hz, 1H), 7.84 (s, 1H), 8.52 (br. s, 1H), 8.78 (d, J=8.7 Hz, 1H); LC-MS (ESI): (MH$^+$) 317.1

Example 10

N-(2-isopropoxy-4-methoxy-phenyl)-5-methyl-pyrrolo[3,2-d]pyrimidin-4-amine

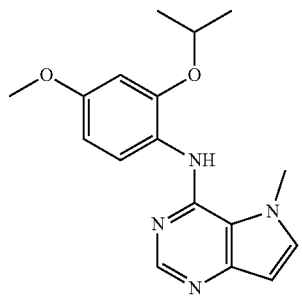 [SMILES: COc1ccc(Nc2ncnc3ccn(C)c23)c(OC(C)C)c1]

Example 10 was prepared analogously to Example 7 with Intermediate 1 and Intermediate 13 to give the desired product (34% yield); $^1$H NMR (400 MHz, CHLOROFORM-d) δ ppm 1.41 (d, J=6.0 Hz, 6H), 3.83 (s, 3H), 4.18 (s, 3H), 4.65 (spt, J=6.0 Hz, 1H), 6.51 (d, J=3.2 Hz, 1H), 6.53-6.59 (m, 2H), 7.10 (d, J=2.7 Hz, 1H), 7.66 (br. s, 1H), 8.49 (s, 1H), 8.61 (d, J=8.7 Hz, 1H); LC-MS (ESI): (MH$^+$) 313.2

Example 11

N-[4-fluoro-2-[2-fluoro-1-(fluoromethyl)ethoxy]phenyl]-5-methyl-pyrrolo[3,2-d]pyrimidin-4-amine

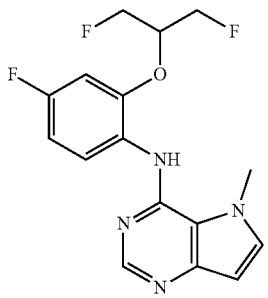

Example 11 was prepared analogously to Example 7 with Intermediate 1 and 4-fluoro-2-[2-fluoro-1-(fluoromethyl)ethoxy]aniline to give the desired product (7.3 mg, 7%); $^1$H NMR (400 MHz, CHLOROFORM-d) δ ppm 4.15 (s, 3H), 4.68 (q, J=1.98 Hz, 3H), 4.77-4.84 (m, 2H), 6.50-6.56 (m, 1H), 6.79 (dd, J=9.62, 2.75 Hz, 1H), 6.86 (ddd, J=9.16, 8.24, 2.75 Hz, 1H), 7.13 (d, J=3.21 Hz, 1H), 7.65 (br. s, 1H), 8.49 (s, 1H), 8.68-8.77 (m, 1H); LC-MS (ESI): (MH$^+$) 337

Example 12

4-[5-fluoro-2-[(5-methylpyrrolo[3,2-d]pyrimidin-4-yl)amino]phenoxy]cyclohexanol

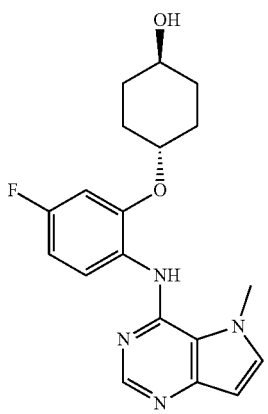 [SMILES: Cn1ccc2ncnc(Nc3ccc(F)cc3O[C@H]3CC[C@H](O)CC3)c21]

Example 12 was prepared analogously to Example 7 with Intermediate 1 and 4-(2-amino-5-fluoro-phenoxy)cyclohexanol to give the desired product (12.9 mg, 12%); $^1$H NMR (400 MHz, CHLOROFORM-d) δ ppm 1.46-1.60 (m, 4H), 1.54 (s, 1H), 2.02-2.14 (m, 2H), 2.19-2.33 (m, 2H), 3.73-3.84 (m, 1H), 4.18 (s, 3H), 4.28-4.40 (m, 1H), 6.55 (d, J=2.75 Hz, 1H), 6.70 (dd, J=10.07, 2.75 Hz, 1H), 6.75 (td, J=8.70, 2.75 Hz, 1H), 7.14 (d, J=3.21 Hz, 1H), 7.61 (s, 1H), 8.50 (s, 1H), 8.63-8.70 (m, 1H), 8.67 (s, 1H); LC-MS (ESI): (MH$^+$) 357.

Example 13

N-(4-fluoro-2-tetrahydropyran-4-yloxy-phenyl)-5-methyl-pyrrolo[3,2-d]pyrimidin-4-amine

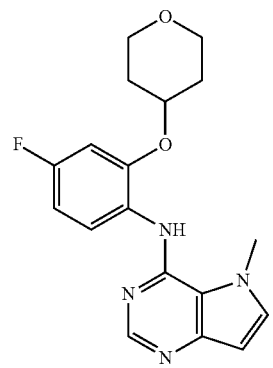 [SMILES: Cn1ccc2ncnc(Nc3ccc(F)cc3OC3CCOCC3)c21]

Example 13 was prepared analogously to Example 7 with Intermediate 1 and 4-fluoro-2-tetrahydropyran-4-yloxy-aniline to give the desired product (18.5 mg, 18%). $^1$H NMR (400 MHz, CHLOROFORM-d) δ ppm 1.75 (dtd, J=13.51, 9.50, 9.50, 4.12 Hz, 2H), 2.10-2.19 (m, 2H), 3.56 (ddd, J=12.14, 10.07, 2.52 Hz, 2H), 3.97-4.04 (m, 2H), 4.18 (s, 3H), 4.49-4.57 (m, 1H), 6.55 (d, J=3.21 Hz, 1H), 6.69 (dd, J=10.07, 2.75 Hz, 1H), 6.75 (ddd, J=9.16, 8.24, 2.75 Hz, 1H), 7.11-7.16 (m, 1H), 7.58-7.69 (m, 1H), 8.50 (s, 1H), 8.67 (dd, J=9.16, 6.41 Hz, 1H); LC-MS (ESI): (MH$^+$) 343.

Example 14

N-(1H-indazol-5-yl)-5-methyl-pyrrolo[3,2-d]pyrimidin-4-amine

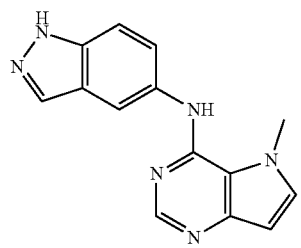 [SMILES: Cn1ccc2ncnc(Nc3ccc4[nH]ncc4c3)c21]

Example 14 was prepared analogously to Example 7 with Intermediate 1 and 5-aminoindazole to give the desired product (24 mg, 30%); $^1$H NMR (400 MHz, DMSO-d$_6$) δ ppm 4.16 (s, 3H), 6.40 (d, J=3.21 Hz, 1H), 7.51 (d, J=0.92 Hz, 2H), 7.53 (d, J=3.21 Hz, 1H), 7.93-7.98 (m, 1H), 8.01-8.06 (m, 1H), 8.18 (s, 1H), 8.40 (br. s., 1H); LC-MS (ESI): (MH$^+$) 357.2

Examples 15-24

Examples 15-24 were prepared analogously to Example 7 from intermediate 1 and the appropriate amine.

| EXAMPLE | STRUCTURE | NAME | m/z (ES + APCI)+ [M + H] |
|---|---|---|---|
| 15 | 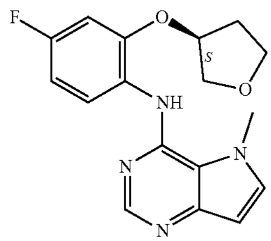 | N-[4-fluoro-2-[(3S)-tetrahydrofuran-3-yl]oxyphenyl]-5-methyl-pyrrolo[3,2-d]pyrimidin-4-amine | 329.2 |
| 16 | 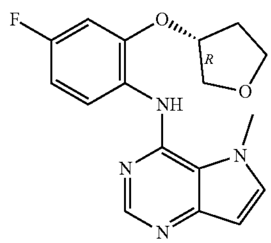 | N-[4-fluoro-2-[(3R)-tetrahydrofuran-3-yl]oxyphenyl]-5-methyl-pyrrolo[3,2-d]pyrimidin-4-amine | 329.2 |
| 17 | 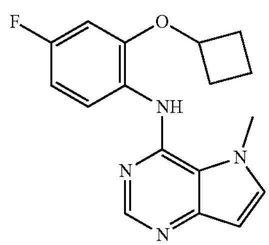 [SMILES: Cn1ccc2ncnc(Nc3ccc(F)cc3OC3CCC3)c21] | N-[2-(cyclobutoxy)-4-fluorophenyl]-5-methyl-pyrrolo[3,2-d]pyrimidin-4-amine | 313.1 |
| 18 | 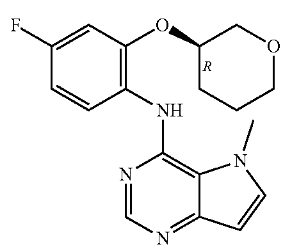 | N-[4-fluoro-2-[(3R)-tetrahydropyran-3-yl]oxyphenyl]-5-methyl-pyrrolo[3,2-d]pyrimidin-4-amine | 343.1 |
| 19 | 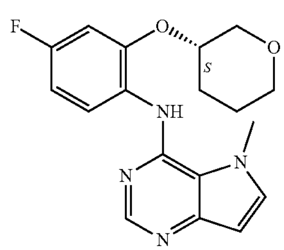 | N-[4-fluoro-2-[(3S)-tetrahydropyran-3-yl]oxyphenyl]-5-methyl-pyrrolo[3,2-d]pyrimidin-4-amine | 343.2 |
| 20 | 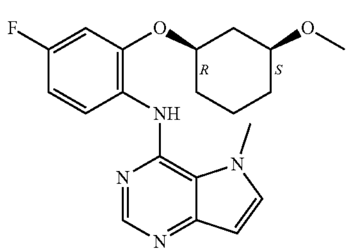 | N-[4-fluoro-2-[(1R,3S)-3-methoxycyclohexoxy]phenyl]-5-methyl-pyrrolo[3,2-d]pyrimidin-4-amine | 371.2 |

| EXAMPLE | STRUCTURE | NAME | m/z (ES + APCI)+ [M + H] |
|---|---|---|---|
| 21 | 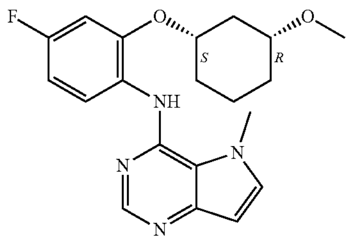 | N-[4-fluoro-2-[(1S,3R)-3-methoxycyclohexoxy]phenyl]-5-methyl-pyrrolo[3,2-d]pyrimidin-4-amine | 371.2 |
| 22 | 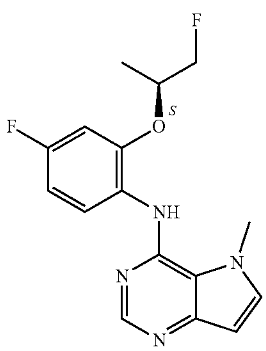 | N-[4-fluoro-2-[(1S)-2-fluoro-1-methyl-ethoxy]phenyl]-5-methyl-pyrrolo[3,2-d]pyrimidin-4-amine | 319.3 |
| 23 | 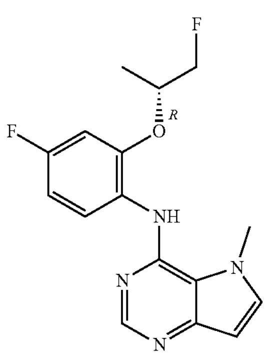 | N-[4-fluoro-2-[(1R)-2-fluoro-1-methyl-ethoxy]phenyl]-5-methyl-pyrrolo[3,2-d]pyrimidin-4-amine | 319.3 |
| 24 | 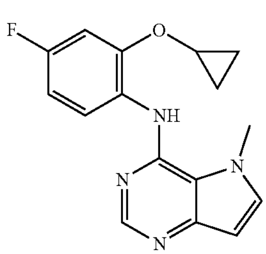 [SMILES: Cn1ccc2ncnc(Nc3ccc(F)cc3OC3CC3)c21] | N-[2-(cyclopropoxy)-4-fluoro-phenyl]-5-methyl-pyrrolo[3,2-d]pyrimidin-4-amine | 299.1 |

Example 25

N-[2-(cyclopentyloxy)-4-fluorophenyl]-5-methyl-5H-pyrrolo[3,2-d]pyrimidin-4-amine

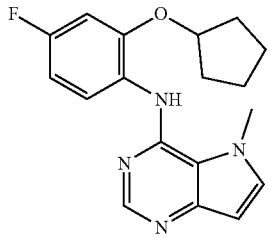 [SMILES: Cn1ccc2ncnc(Nc3ccc(F)cc3OC3CCCC3)c21]

4-Chloro-5-methyl-5H-pyrrolo[3,2-d]pyrimidine (60 mg, 0.36 mmol), p-TsOH.H$_2$O (6.8 mg, 0.04 mmol), 2-(cyclopentyloxy)-4-fluoroaniline (70 mg, 0.36 mmol) and IPA (1 mL) were placed in a microwave reactor vial. The vial was sealed and irradiated at 140° C. in a Biotage I-60 microwave reactor for 15 minutes. The reaction mixture was concentrated, then dissolved in 10% MeOH in DCM and eluted through an Isolute-NH$_2$ cartridge. Purified by preparative HPLC to give a white solid (48 mg, 41%). $^1$H NMR (400 MHz, DMSO-d$_6$) δ ppm 1.55-1.67 (m, 4H), 1.73-1.80 (m, 2H), 1.90-1.97 (m, 2H), 4.21 (s, 3H), 4.94-4.98 (m, 1H), 6.41 (d, J=2.7 Hz, 1H), 6.76-6.81 (m, 1H), 6.99 (dd, J=11.0, 2.7 Hz, 1H), 7.54 (d, J=2.7 Hz, 1H), 7.95-7.97 (m, 1H), 8.27 (s, 1H), 8.43 (dd, J=9.2, 6.4 Hz, 1H); m/z (ES+APCI)$^+$ 327 [M+H]$^+$.

Examples 26-35

Examples 26-31 were prepared analogously to Example 25 from Intermediate 1 and the appropriate amine. Examples 32-35 were carried out in a similar manner to Example 25 except the reactions were carried out using conventional heating at 60° C. rather than microwave heating.

| Example | Structure | Name | LCMS retention time | M + H |
|---|---|---|---|---|
| 26 | 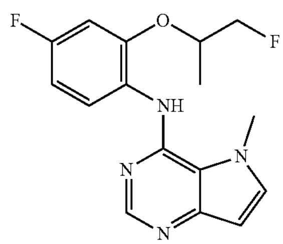 [SMILES: CC(CF)Oc1cc(F)ccc1Nc1ncnc2ccn(C)c12] | Racemic-N-[4-fluoro-2-(2-fluoro-1-methyl-ethoxy)phenyl]-5-methyl-pyrrolo[3,2-d]pyrimidin-4-amine | 1.23a | 319.1 |
| 27 | 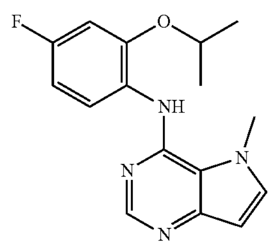 [SMILES: CC(C)Oc1cc(F)ccc1Nc1ncnc2ccn(C)c12] | N-(4-fluoro-2-isopropoxy-phenyl)-5-methyl-pyrrolo[3,2-d]pyrimidin-4-amine | 1.63b | 301.1 |
| 28 | 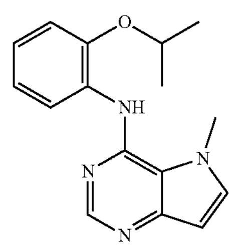 [SMILES: CC(C)Oc1ccccc1Nc1ncnc2ccn(C)c12] | N-(2-isopropoxyphenyl)-5-methyl-pyrrolo[3,2-d]pyrimidin-4-amine | 2.25c | 283.2 |
| 29 | 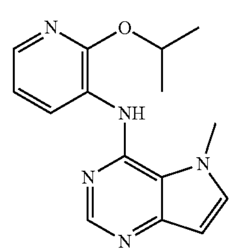 [SMILES: CC(C)Oc1ncccc1Nc1ncnc2ccn(C)c12] | N-(2-isopropoxy-3-pyridyl)-5-methyl-pyrrolo[3,2-d]pyrimidin-4-amine | 2.19c | 284.2 |

-continued

| Example | Structure | Name | LCMS retention time | M + H |
|---|---|---|---|---|
| 30 | 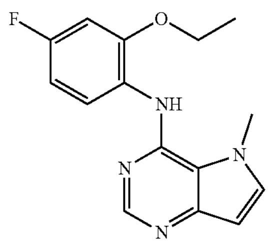 [SMILES: CCOc1cc(F)ccc1Nc1ncnc2ccn(C)c12] | N-(2-ethoxy-4-fluoro-phenyl)-5-methyl-pyrrolo[3,2-d]pyrimidin-4-amine | 2.16c | 287.3 |
| 31 | 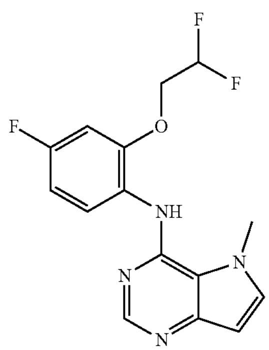 [SMILES: Cn1ccc2ncnc(Nc3ccc(F)cc3OCC(F)F)c21] | N-[2-(2,2-difluoroethoxy)-4-fluoro-phenyl]-5-methyl-pyrrolo[3,2-d]pyrimidin-4-amine | 1.95c | 323.1 |
| 32 | 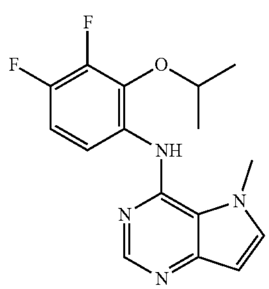 [SMILES: CC(C)Oc1c(Nc2ncnc3ccn(C)c23)ccc(F)c1F] | N-(3,4-difluoro-2-isopropoxy-phenyl)-5-methyl-pyrrolo[3,2-d]pyrimidin-4-amine | 2.24c | 319.1 |
| 33 | 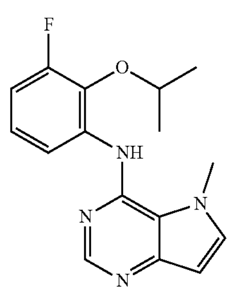 [SMILES: CC(C)Oc1c(F)cccc1Nc1ncnc2ccn(C)c12] | N-(3-fluoro-2-isopropoxy-phenyl)-5-methyl-pyrrolo[3,2-d]pyrimidin-4-amine | 2.17c | 301.2 |
| 34 | 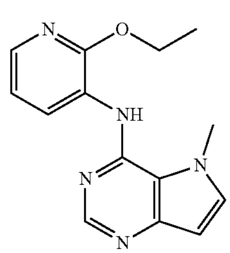 [SMILES: CCOc1ncccc1Nc1ncnc2ccn(C)c12] | N-(2-ethoxy-3-pyridyl)-5-methyl-pyrrolo[3,2-d]pyrimidin-4-amine | 2.00c | 270.1 |

| Example | Structure | Name | LCMS retention time | M + H |
|---|---|---|---|---|
| 35 | 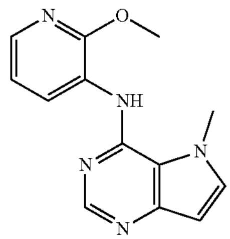 [SMILES: COc1ncccc1Nc1ncnc2ccn(C)c12] | N-(2-methoxy-3-pyridyl)-5-methyl-pyrrolo[3,2-d]pyrimidin-4-amine | 1.15c | 256.2 |

LCMS carried out using an Agilent 6120 quadrupole LC-MS with Xbridge C18 column (3.5 µm particle size and 4.6×30 mm) and a diode array UV detector. Flow rate 3 ml/min; [a]Run time: 3.2 min: Solvent A: 0.1% Trifluoro Acetic acid in water, Solvent B: Acetonitrile; Gradient—10-100% Acetonitrile; Gradient time: 2.35 min. [b]Run time: 3.2 min: Solvent A: 0.1% Ammonium Hydroxide in water, Solvent B: Acetonitrile; Gradient—10-100% Acetonitrile; Gradient time: 2.35 min. [c]Run time: 3.2 min: Solvent A: 0.1% Ammonium Hydroxide in water, Solvent B: Methanol; Gradient—10-100% Methanol; Gradient time: 2.35 min.

Example 36

(1S,2S)-2-[5-fluoro-2-[(5-methylpyrrolo[3,2-d]pyrimidin-4-yl)amino]phenoxy]cyclohexanol

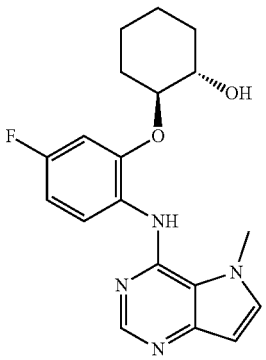 [SMILES: Cn1ccc2ncnc(Nc3ccc(F)cc3O[C@H]3CCCC[C@@H]3O)c21]

Intermediate 20 (81 mg, 0.36 mmol), 4-chloro-5-methyl-pyrrolo[3,2-d]pyrimidine (60 mg, 0.36 mmol), pTsOH.H$_2$O (7 mg, 0.036 mmol) and IPA (2 ml) were combined in a sealed microwave reactor vial and heated at 140° C. in a Biotage microwave reactor for 15 minutes. The mixture was evaporated and purified by preparative LCMS to give a white solid (45 mg, 35%); $^1$H NMR (400 MHz, DMSO-d$_6$) δ ppm 1.12-1.40 (m, 4H), 1.53-1.63 (m, 2H), 1.80-1.89 (m, 1H), 2.01-2.13 (m, 1H), 3.44-3.54 (m, 1H), 4.02-4.12 (m, 1H), 4.18 (s, 3H), 5.08 (d, J=4.58 Hz, 1H), 6.36-6.41 (m, 1H), 6.72-6.80 (m, 1H), 7.04-7.12 (m, 1H), 7.51-7.57 (m, 1H), 8.08-8.15 (m, 1H), 8.26 (s, 1H), 8.38-8.48 (m, 1H); m/z (ES+APCI)$^+$ 357.2

Example 37

N-[4-fluoro-2-[(1S,2S)-2-methoxycyclohexoxy]phenyl]-5-methyl-pyrrolo[3,2-d]pyrimidin-4-amine

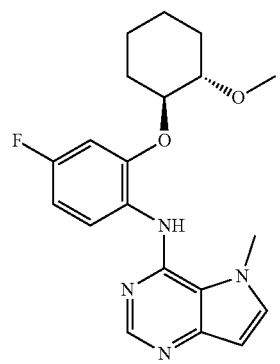 [SMILES: CO[C@H]1CCCC[C@@H]1Oc1cc(F)ccc1Nc1ncnc2ccn(C)c12]

Example 37 was prepare analogously to Example 36 from Intermediate 29 and 4-chloro-5-methyl-pyrrolo[3,2-d]pyrimidine to give a white solid (30 mg, 22%); $^1$H NMR (400 MHz, DMSO-d$_6$) δ ppm 1.09-1.40 (m, 4H), 1.47-1.64 (m, 2H), 1.92-2.09 (m, 2H), 3.18 (s, 3H), 3.20-3.27 (m, 1H), 4.17 (s, 3H), 4.24-4.39 (m, 1H), 6.34-6.41 (m, 1H), 6.70-6.80 (m, 1H), 7.02-7.13 (m, 1H), 7.49-7.54 (m, 1H), 7.88-7.99 (m, 1H), 8.19-8.25 (m, 1H), 8.27-8.35 (m, 1H); (MH$^+$) 371

Example 38

N-[4-fluoro-2-[(1R,2R)-2-methoxycyclohexoxy]phenyl]-5-methyl-pyrrolo[3,2-d]pyrimidin-4-amine

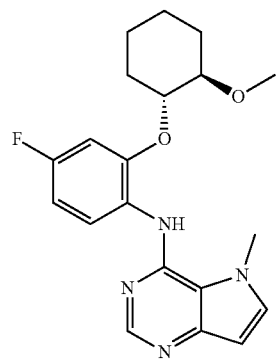 [SMILES: CO[C@@H]1CCCC[C@H]1Oc1cc(F)ccc1Nc1ncnc2ccn(C)c12]

Example 38 was prepare analogously to Example 36 from Intermediate 18 and 4-chloro-5-methyl-pyrrolo[3,2-d]pyrimidine to give a white solid (48 mg, 36%); $^1$H NMR (400 MHz, DMSO-d$_6$) δ ppm 1.11-1.41 (m, 4H), 1.47-1.64 (m, 2H), 1.98 (t, J=9.39 Hz, 2H), 3.18 (s, 3H), 3.20-3.26 (m, 1H), 4.17 (s, 3H), 4.26-4.37 (m, 1H), 6.34-6.40 (m, 1H), 6.72-6.80 (m, 1H), 7.04-7.11 (m, 1H), 7.52 (d, J=3.21 Hz, 1H), 7.96 (s, 1H), 8.23 (s, 1H), 8.26-8.35 (m, 1H); (MH$^+$) 371.

Example 39

N-[3-(dimethylamino)propyl]-4-(5-fluoroindolin-1-yl)-5H-pyrrolo[3,2-d]pyrimidine-6-carboxamide

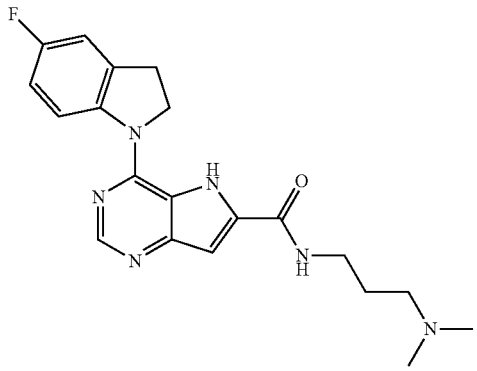 [SMILES: CN(C)CCCNC(=O)c1cc2ncnc(N3CCc4cc(F)ccc43)c2[nH]1]

Step 1 (4-chloro-5-(p-tolylsulfonyl)pyrrolo[3,2-d]pyrimidine)

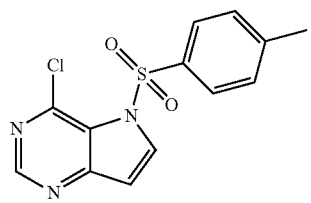 [SMILES: Cc1ccc(S(=O)(=O)n2ccc3ncnc(Cl)c32)cc1]

NaH (60% in mineral oil, 0.17 g, 4.23 mmol) was added portion wise to a stirred solution of 4-chloro-5H-pyrrolopyrimidine (0.5 g, 3.26 mmol) in DMF (20 mL) at 0° C. under N$_2$. The solution was stirred at 0° C. for 10 minutes, then p-toluenesulfonyl chloride (683 mg, 0.04 mmol) was added and the reaction stirred at rt for 4 h. The reaction mixture was quenched at 0° C. with water (30 mL) and extracted with DCM (×3). The combined organics were washed with water (3×30 mL), brine, dried (MgSO$_4$) and then solvent was removed in vacuo to give the desired product as a white solid (0.63 g, 48%).

Step 2 (ethyl 4-chloro-5-(p-tolylsulfonyl)pyrrolo[3,2-d]pyrimidine-6-carboxylate)

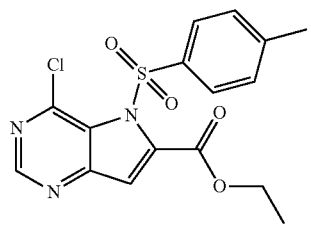 [SMILES: CCOC(=O)c1cc2ncnc(Cl)c2n1S(=O)(=O)c1ccc(C)cc1]

n-Butyllithium (1.6 M in hexanes, 1.38 mL, 2.21 mmol) was added dropwise to a stirred solution of 4-chloro-5-(p-tolylsulfonyl)pyrrolo[3,2-d]pyrimidine (0.4 g, 1.30 mmol) in THF (25 mL) at −78° C. under N$_2$. The solution was stirred at −78° C. for 2 h, and then ethyl chloroformate was added (0.27 μL, 2.87 mmol). The reaction was stirred at −78° C. for 1 h then warmed to 0° C. and stirred for 1 h. The mixture was quenched with sat. NH$_4$Cl (aq), extracted with EtOAc (×2), and the combined organic layers were washed with brine, dried (MgSO$_4$) and evaporated. Purification by flash chromatography eluting with 10-40% EtOAc/petroleum ether gave a yellow oil (0.34 g, 70%).

Step 3 (ethyl 4-(5-fluoroindolin-1-yl)-5H-pyrrolo[3,2-d]pyrimidine-6-carboxylate)

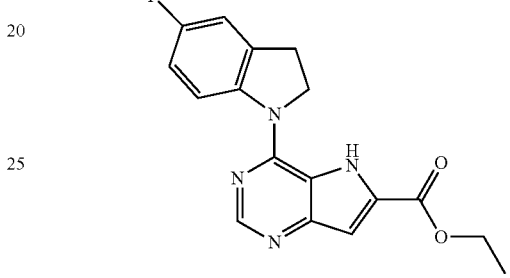

Ethyl 4-chloro-5-(p-tolylsulfonyl)pyrrolo[3,2-d]pyrimidine-6-carboxylate (200 mg, 0.53 mmol), 5-fluoroindoline (217 mg, 1.58 mmol), p-TsOH.H$_2$O (10 mg, 0.05 mmol) and IPA (2 mL) were placed in a sealed microwave reactor vial and the mixture was irradiated at 80° C. for 20 minutes. The reaction mixture was loaded onto a 2 g Isolute-NH$_2$ cartridge, eluted with DCM:MeOH (1:1) and the filtrate was concentrated. Purification by flash chromatography eluting with 0-5% 2M NH$_3$ in MeOH/DCM gave a yellow solid (160 mg, 93%).

Step 4 (ethyl 4-(5-fluoroindolin-1-yl)-5-(2-trimethylsilylethoxymethyl)pyrrolo[3,2-d]pyrimidine-6-carboxylate)

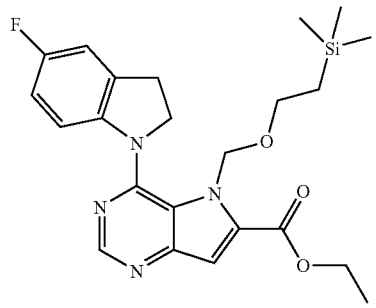 [SMILES: CCOC(=O)c1cc2ncnc(N3CCc4cc(F)ccc43)c2n1COCC[Si](C)(C)C]

NaH (60% in mineral oil, 27 mg, 0.67 mmol) was added portion wise to a stirred solution of ethyl 4-(5-fluoroindolin-1-yl)-5H-pyrrolo[3,2-d]pyrimidine-6-carboxylate (137 mg, 0.42 mmol) in DMF (5 mL) at 0° C. under N$_2$. The mixture was stirred at rt for 45 minutes, then SEMCl (111 μL, 0.63 mmol) was added and the mixture was stirred at rt for 18 h. The reaction mixture was quenched with water which gave a yellow precipitate. The solid was filtered, washed with water and then dried by azeotroping with Toluene/MeCN. The desired product was isolated as a yellow solid with impurities (230 mg).

Step 5 (4-(5-fluoroindolin-1-yl)-5-(2-trimethylsilylethoxymethyl)pyrrolo[3,2-d]pyrimidine-6-carboxylic acid)

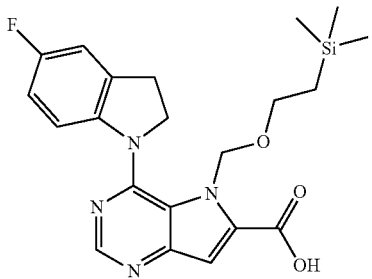 [SMILES: C[Si](C)(C)CCOCn1c(C(=O)O)cc2ncnc(N3CCc4cc(F)ccc43)c21]

To a stirred solution of ethyl 4-(5-fluoroindolin-1-yl)-5-(2-trimethylsilylethoxymethyl)-pyrrolo[3,2-d]pyrimidine-6-carboxylate (230 mg, 0.50 mmol) in EtOH (10 mL) and THF (10 mL) was added 1N NaOH (1.2 mL, 1.2 mmol). The reaction mixture was stirred at rt for 18 h, and then acidified with 2M HCl and evaporated to dryness. The crude product was taken up in water, filtered and dried to give an off-white solid (216 mg, 100%).

Step 6 (N-[3-(dimethylamino)propyl]-4-(5-fluoroindolin-1-yl)-5-(2-trimethylsilylethoxymethyl)pyrrolo[3,2-d]pyrimidine-6-carboxamide)

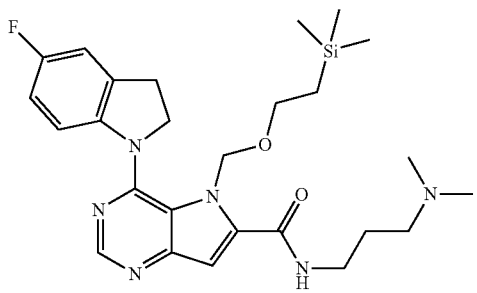 [SMILES: CN(C)CCCNC(=O)c1cc2ncnc(N3CCc4cc(F)ccc43)c2n1COCC[Si](C)(C)C]

4-(5-fluoroindolin-1-yl)-5-(2-trimethylsilylethoxymethyl)pyrrolo[3,2-d]pyrimidine-6-carboxylic acid (220 mg, 0.51 mmol), HATU (231 mg, 0.61 mmol), DIPEA (0.49 mL, 2.80 mmol) and N,N-dimethylaminopropylamine (39 µL, 0.47 mmol) were combined in DCM (3 mL) and DMF (3 mL) and stirred at rt for 18 h. The reaction mixture was diluted with water, the phases were separated and the aqueous extracted with DCM (×2). After evaporation, the crude product was dissolved in EtOAc and washed with H$_2$O (×2), brine, dried (MgSO$_4$) and concentrated. Purification using by flash chromatography, eluting with 10-20% 2M NH$_3$ in MeOH/DCM gave 120 mg, 46% of product which was used in the next step.

Step 7 (N-[3-(dimethylamino)propyl]-4-(5-fluoroindolin-1-yl)-5H-pyrrolo[3,2-d]pyrimidine-6-carboxamide Example 39)

To a solution of N-[3-(dimethylamino)propyl]-4(5-fluoroindolin-1-yl)-5-(2-trimethylsilyl-ethoxymethyl)-pyrrolo[3,2-d]pyrimidine-6-carboxamide (70 mg, 0.14 mmol) in THF (5 ml) was added ethylene diamine (14 µL, 0.20 mmol) and 1M solution of TBAF in THF (0.17 ml, 0.16 mmol). The mixture was refluxed for 2 hours, cooled, concentrated and purified via HPLC to give Example 39 (8 mg, 15%); $^1$H NMR (400 MHz, CHLOROFORM-d) δ ppm 1.79 (quin, J=5.7 Hz, 2H), 2.38 (s, 6H), 2.59 (t, J=5.50 Hz, 2H), 3.32 (t, J=8.24 Hz, 2H), 3.59 (q, J=5.50 Hz, 2H), 4.59 (t, 1=8.47 Hz, 2H), 6.76 (s, 1H), 6.90-7.00 (m, 2H), 8.16 (m, J=8.70 Hz, 1H), 8.54-8.60 (m, 1H), 9.33 (br. s., 1H), 9.43 (br. t, J=1.00 Hz, 1H); LC-MS (ESI): (MH$^+$) 383.1

Example 40

N-[3-(dimethylamino)propyl]-4-{[4-fluoro-2-(propan-2-yloxy)phenyl]amino}-5-methyl-5H-pyrrolo[3,2-d]pyrimidine-6-carboxamide

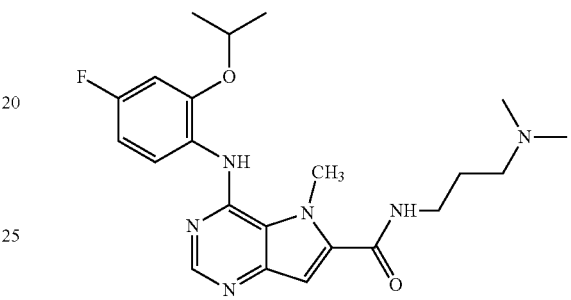

A mixture of Intermediate 31 (30 mg, 0.087 mmol), 3-(dimethylamino)-1-propylamine (11 µl, 0.087 mmol) and HOBt (12 mg, 0.087 mmol) in DCM (2 ml) was stirred at rt for 10 minutes. EDC hydrochloride (17 mg, 0.087 mmol) was added and the reaction mixture was stirred at rt overnight. The reaction mixture was then passed through a SCX cartridge eluting with MeOH. The product was eluted with 2M NH$_3$ in MeOH and the eluent was concentrated to dryness. The residue was pre-absorbed on to silica gel prior to purification by flash chromatography on silica gel eluting with 10:1 DCM:2 M NH$_3$ in MeOH to give a yellow solid. Trituration in Et$_2$O to provide a white solid (15 mg, 40%). $^1$H NMR (400 MHz, DMSO-d$_6$) δ ppm 1.29 (d, J=5.95 Hz, 6H), 1.67 (quin, J=7.10 Hz, 2H), 2.14 (s, 6H), 2.27 (t, J=7.10 Hz, 2H), 3.22-3.34 (m, 2H), 4.38 (s, 3H), 4.75 (dt, J=12.25, 6.01 Hz, 1H), 6.80 (td, J=8.70, 2.75 Hz, 1H), 6.93 (s, 1H), 7.06 (dd, J=10.99, 2.75 Hz, 1H), 8.23 (s, 1H), 8.32 (s, 1H), 8.45 (dd, J=8.70, 6.41 Hz, 1H), 8.74 (t, J=5.72 Hz, 1H). m/z (ES+APCI)$^+$: 429 [M+H]$^+$ Example 41

4-{[4-Fluoro-2-(propan-2-yloxy)phonyl]amino}-5-methyl-N-(piperidin-4-ylmethyl)-5H-pyrrolo[3,2-d]pyrimidine-6-carboxamide

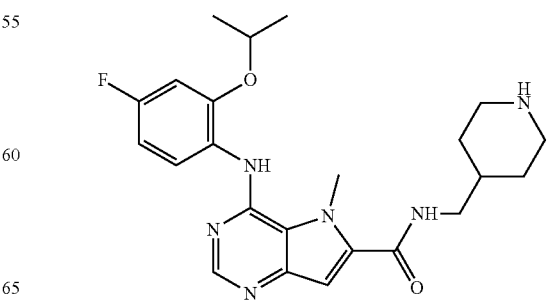

Intermediate 32 (78 mg, 0.144 mmol) in TFA (2 ml) and DCM (6 ml) was stirred at rt for 2 hours. The reaction mixture was then concentrated to dryness. The residue was dissolved in MeOH and passed through a SCX cartridge. The product was eluted with 2 M $NH_3$ in MeOH and the eluent was concentrated. The residue was pre-absorbed on to silica gel prior to purification by flash chromatography on silica gel eluting with 3:1 DCM:2 M $NH_3$ in MeOH to give an off-white solid (42 mg, 66%). $^1$H NMR (400 MHz, DMSO-$d_6$) δ ppm 0.97-1.12 (m, 2H), 1.29 (d, J=5.95 Hz, 6H), 1.55-1.70 (m, 3H), 2.35-2.46 (m, 2H), 2.87-2.97 (m, 2H), 3.13 (t, J=6.18 Hz, 2H), 4.37 (s, 3H), 4.75 (dt, J=12.02, 6.13 Hz, 1H), 6.80 (td, J=8.93, 2.75 Hz, 1H), 6.95 (s, 1H), 7.06 (dd, J=10.99, 2.75 Hz, 1H), 8.22 (s, 1H), 8.32 (s, 1H), 8.45 (dd, J=8.93, 6.64 Hz, 1H), 8.70 (t, J=5.72 Hz, 1H). m/z (ES+APCI)$^+$: 441 [M+H]$^+$ Example 42

4-{[4-Fluoro-2-(propan-2-yloxy)phenyl]amino}-5-methyl-N-[2-(piperazin-1-yl)ethyl]-5H-pyrrolo[3,2-d]pyrimidine-6-carboxamide

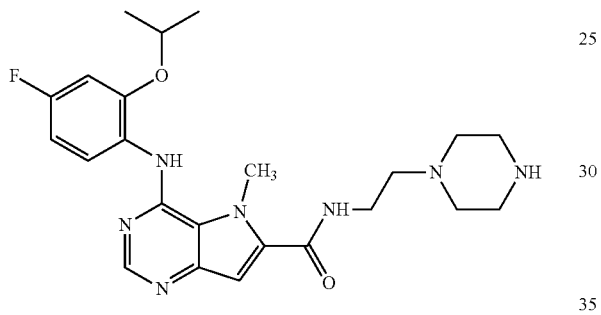

Example 42 was prepared in analogous fashion to Example 41 to give an off-white coloured solid (yield 47%). $^1$H NMR (400 MHz, DMSO-$d_6$) δ ppm 1.29 (d, J=5.95 Hz, 6H), 2.26-2.48 (m, 6H), 2.69 (t, J=4.81 Hz, 4H), 3.27-3.44 (m, 2H), 4.38 (s, 3H), 4.75 (dt, J=12.02, 6.13 Hz, 1H), 6.80 (td, J=8.70, 2.75 Hz, 1H), 6.91 (s, 1H), 7.06 (dd, J=10.99, 2.75 Hz, 1H), 8.23 (s, 1H), 8.32 (s, 1H), 8.45 (dd, J=8.70, 6.41 Hz, 1H), 8.63 (t, J=5.50 Hz, 1H). m/z (ES+APCI)$^+$: 456 [M+H]$^+$ Example 43

7-Chloro-N-[3-(dimethylamino)propyl]-4-{[4-fluoro-2-(propan-2-yloxy)phenyl]amino}-5-methyl-5H-pyrrolo[3,2-d]pyrimidine-6-carboxamide

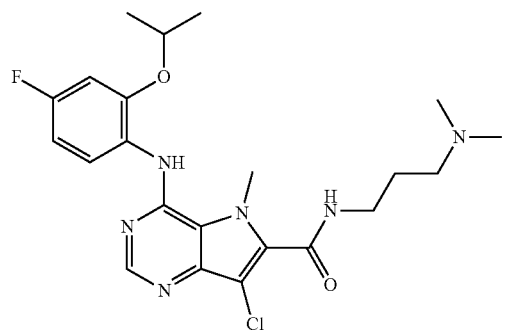 [SMILES: CC(C)Oc1cc(F)ccc1Nc1ncnc2c(Cl)c(C(=O)NCCCN(C)C)n(C)c12]

Example 43 was prepared in analogous fashion to Intermediate 32 from Intermediate 29 to give an off-white solid (yield 43%). $^1$H NMR (400 MHz, DMSO-$d_6$) δ ppm 1.22-1.31 (m, 6H), 1.70 (quin, J=6.98 Hz, 2H), 2.15 (s, 6H), 2.33 (t, J=7.10 Hz, 2H), 3.28-3.40 (m, 2H), 4.73 (dt, J=12.25, 6.01 Hz, 1H), 6.81 (td, J=8.70, 2.75 Hz, 1H), 7.06 (dd, J=10.99, 2.75 Hz, 1H), 8.26 (s, 1H), 8.31 (dd, J=9.16, 6.41 Hz, 1H), 8.35 (s, 1H), 8.81-8.96 (m, 1H). m/z (ES+APCI)$^+$: 463/465 [M+H]$^+$ Example 44

N-[3-(dimethylamino)propyl]-4-(4-fluoro-2-isopropoxy-anilino)-5H-pyrrolo[3,2-d]pyrimidine-6-carboxamide

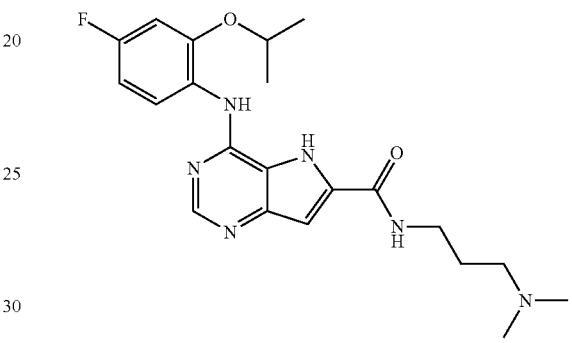

Step 1 (Ethyl 4-(4-fluoro-2-isopropoxy-anilino)-5H-pyrrolo[3,2-d]pyrimidine-6-carboxylate)

4-chloro-5-(p-tolylsulfonyl)pyrrolo[3,2-d]pyrimidine (400 mg, 1.06 mmol), 4-fluoro-2-(propan-2-yloxy)aniline (184 mg, 1.11 mmol), pTsOH.H$_2$O (20 mg, 0.11 mmol) and IPA (1 mL) were irradiated at 100° C. in a Biotage 1-60 microwave reactor for 20 min. The reaction mixture was concentrated, dissolved in 10% MeOH in DCM and eluted through an Isolute-NH$_2$ cartridge. Purification by flash chromatography eluting with 0-50% EtOAc/petroleum ether gave yellow solid (195 mg, 52%).

Step 2 (4-(4-fluoro-2-isopropoxy-anilino)-5H-pyrrolo[3,2-d]pyrimidine-6-carboxylic acid)

To a stirred solution of Ethyl 4-(4-fluoro-2-isopropoxy-anilino)-5H-pyrrolo[3,2-d]pyrimidine-6-carboxylate) (171 mg, 0.48 mmol) in EtOH (5 mL) and THF (5 mL) was added 1N NaOH (2.39 mL, 2.39 mmol). The reaction mixture was heated at 70° C. for 1 h, cooled and concentrated. The crude material was dissolved in water, neutralised with 1M HCl and concentrated under reduced pressure to give a solid (187 mg) which was used in the next step without further purification.

Step 3 N-[3-(dimethylamino)propyl]-4-(4-fluoro-2-isopropoxy-anilino)-5H-pyrrolo[3,2-d]pyrimidine-6-carboxamide 4-(4-fluoro-2-isopropoxy-anilino)-5H-pyrrolo[3,2-d]pyrimidine-6-carboxylic acid (158 mg, 0.47 mmol), HATU (196 mg, 0.52 mmol), DIPEA (0.38 mL, 2.21 mmol) and N,N-dimethylaminopropylamine (46 μL, 0.37 mmol) were combined in DMF (5 mL) and stirred at rt for 18 h. The reaction mixture was concentrated, dissolved in 10% MeOH in DCM and eluted through an Isolute-NH$_2$ cartridge. Purification by flash chromatography eluting with 0-15% 1M NH$_3$ in MeOH/DCM followed by preparative LCMS gave a white solid (17 mg, 11%). $^1$H NMR (400 MHz, CD$_3$OD) δ ppm 1.27-1.40 (m, 6H), 1.77-1.91 (m, 2H), 2.24-2.33 (m, 6H), 2.42-2.48 (m, 2H), 3.37-3.50 (m, 2H), 4.65 (spt, J=6.11 Hz, 1H), 6.61-7.08 (m, 3H), 7.75-8.16 (m, 1H), 8.23 (s, 1H). m/z (ES+APCI)$^+$: 415 [M+H]$^+$ Example 45

N-(4-fluoro-2-isopropoxy-phenyl)-5H-pyrrolo[3,2-d]pyrimidin-4-amine

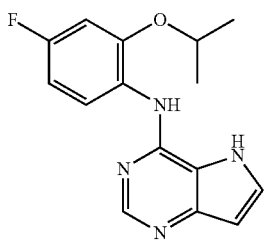 [SMILES: CC(C)Oc1cc(F)ccc1Nc1ncnc2cc[nH]c12]

4-Chloro-5H-pyrrolo[3,2-d]pyrimidin-4-amine (75 mg, 0.49 mmol), 4-fluoro-2-isopropoxyaniline (99 mg, 0.59 mmol), isopropanol (2 ml) and 4M HCl in dioxane (0.1 ml) were combined in a vial and irradiated in a Biotage Initiator 60 microwave reactor at 140° C. for 30 min. The mixture was concentrated and purified by preparative HPLC to give an off white solid (25 mg, 18%). $^1$H NMR (400 MHz, DMSO-d$_6$) δ ppm 0.46 (d, J=6.41 Hz, 6H), 3.78-3.88 (m, 1H), 5.63 (dd, J=2.75, 1.83 Hz, 1H), 5.92-5.98 (m, 1H), 6.20 (dd, J=10.99, 2.75 Hz, 1H), 6.80-6.82 (m, 1H), 7.21 (dd, J=8.93, 6.64 Hz, 1H), 7.37 (s, 1H), 7.38-7.40 (m, 1H), 10.78 (br. s., 1H); m/z (ES+APCI)$^+$: 287 [M+H]$^+$ Example 46

4-(5-Fluoroindolin-1-yl)-5H-pyrrolo[3,2-d]pyrimidine

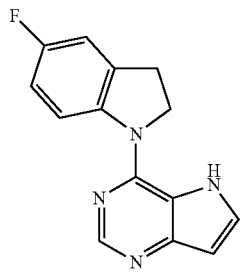 [SMILES: Fc1ccc2c(c1)CCN2c1ncnc2cc[nH]c12]

Prepared analogously to Example 45 by reacting 5-fluoroindoline with 4-Chloro-5H-pyrrolo[3,2-d]pyrimidin-4-amine to give a pale brown solid.); m/z (ES+APCI)$^+$ $^1$H NMR (400 MHz, DMSO-d$_6$) δ ppm 3.28-3.37 (m, 2H), 4.60 (t, J=8.70 Hz, 2H), 6.51 (dd, J=3.21, 1.83 Hz, 1H), 6.97-7.04 (m, 1H), 7.11-7.16 (m, 1H), 7.62 (t, J=3.21 Hz, 1H), 8.34-8.42 (m, 2H), 11.42 (br. s., 1H): 255 [M+H]$^+$ MNK1 and 2 Biochemical IC50 Assays The effects of compounds on MNK1 and MNK2 activity was determined in a biochemical assay by monitoring the phosphorylation of Serine/Thereonine Kinase peptide 5FAM-RRRLSSLRA-NH2. The phosphorylated peptide product and unphosphorylated peptide substrate were detected using a Caliper Mobility Shift Assay using the Caliper LabChip EZ Reader II.

The Caliper Mobility Shift Assay technology is based on the utilisation of a microfludic chip to measure the conversion of a fluorescent non-phosphorylated peptide substrate to phosphorylated product by electrophoresis separation of substrate and product and detection via Laser-induced fluorescence. The LabChip EZ Reader software calculates the relative heights of substrate and product peaks and reports the peak ratio (Product peak (P) divided by the sum of Product peak(P) and Substrate peak(S)). The percent-conversion is calculated as 100×[(P/(P+S)]. All assays were set up to run in the linear phase with a maximum of 10 percent substrate conversion.

Reagents

The enzymes, MNK1 and MNK2 used for all screening activities were sourced from Carna Biosciences (Product codes 02-145 and 02-146 respectively). These were N-terminal GST fusion proteins expressed in baculovirus expression system and purified by glutathione sepharose affinity chromatography. Specifically these constructs comprised of Full-length human MNK1 [1-424(end) amino acids and T344D of accession number BAA19885.1] and Full-length human MNK2 [1-465(end) amino acids and T379D of accession number NP_951009.1]. A FAM-labelled generic ser/thr kinase peptide substrate was purchased from Anaspec—5-FAM-RRRLSSLRA-NH$_2$. Detection reagents for use on the Caliper—Labchip EZ reader 12-sipper (cat No. 760404), separating buffer and coating reagent-8 (CR-8)—were purchased from Perkin Elmer. All other assay reagents were sourced from Sigma.

MNK1 Assay

Compounds were serially diluted in DMSO to generate a 10-point half log dilution curve with a final top concentration of 100 uM in the assay. Reactions were set up in a total volume of 30 uL in polypropylene-384-well U-bottomed plates (Thermo Scientific 4340). Compounds were pre-incubated with enzyme and peptide in reaction buffer for 30 mins prior to addition of ATP to initiate the reaction. Final assay concentrations were 3 nM MNK1, 2 uM peptide substrate, 50 uM ATP, 50 mM Hepes pH 7.0, 0.01% BSA, 10 mM MgCl$_2$, 1 mM dithiothrietol. Plates were incubated at room temperature and the reaction was stopped by the addition of 2 volumes (60 µl) of 50 mM EDTA at a point where approximately 10% substrate conversion had been achieved.

The assay incubation times were adjusted depending on the concentration of ATP used. Assays were performed at low (50 uM) and high (1 mM) ATP. The low ATP values were selected to run at Km conditions for the standard assay to allow relative potencies to be compared across other kinases. The high ATP concentration was selected as representative of cellular ATP concentrations, and for an indication of ATP competition, where a significant shift (greater than half log) in apparent potency would be expected compared to Km conditions. All IC50 values reported are the average of at least two independent experiments.

MNK2 Assay

Reactions were performed as above using 10 nM MNK2 in the assay. Standard assays contained 50 uM ATP and high concentration ATP assays contained 1 mM ATP. Time to achieve 10% conversion varied. All other conditions were the same.

MNK Cellular Activity Phospho-eIF4E Detection Assay

MNK activity in cells was measured by monitoring the phosphorylation of eIF4E at ser209, the known endogenous substrate of MNK1/2, in cell lysates. An amplified luminescent proximity homogeneous assay (Alphascreen Surefire p-eIF4E kit, Perkin Elmer) was used to enable dose-dependent responses to be quantified in a 384 format cell based assay. The assay detection is based on the formation of sandwich antibody complexes coupled to donor and acceptor beads. Excitation at 680 nm causes the transfer of a singlet oxygen species between donor and acceptor beads when they are in close proximity by binding to the analyte (p-eIF4a-ser209), which results in the emission of light at 520-620 nm.

A number of cancer cell lines were investigated, and the MV4.11 cell line (ATCC, CRL-9591), a biphenotypic B myelomonocytic leukemia cell line was selected for routine profiling of compounds. Compound dilutions were prepared in IMDM-10% FBS medium to generate a 10 point half log serial dilution starting at a final top concentration in the assay of 30 uM. Frozen cells were suspended in IMDM-10% FBS medium at a concentration of $1.2 \times 10^6$/ml. 4 ul (4,800 cells per well) was dispensed into each well of a 384-tissue culture Proxiplate plates (Perkin Elmer 6008238) and 4 ul of compound media dilution was added to the cells and incubated for 1.5 hr at 37 C, 5% $CO_2$. Cells were then lysed and the Aphascreen Surefire protocol followed according to manufacturer's recommendations. 8 ul Acceptor beads (1:50 dilution in kit activation buffer) was added to lysate, shaken 150 rpm for 2 min and incubated for 1.5 hr at room temperature. 3 ul Donor beads (1:20 dilution in kit dilution buffer) were then added, shaken 150 rpm for 2 min and incubated for a further 1.5 hr at room temperature after which the plates were read on Pherastar FS using Alphascreen optic module.

Data were normalised relative to untreated DMSO only controls and curves repeated in duplicate within experiments. Data reported are averages of at least 2 independent experiments.

Kinase Selectivity Screen

Kinase screening was carried out using commercially available reagents and protocols, by way of a third party kinase profiling service, such as Eurofins KinaseProfiler™ (see wvvw.eurofins.com/pharmadiscovery) or similar such service provider.

The results of a kinase selectivity screen for Example 40 are shown in Table 2. Data are expressed as % inhibition of each specific kinase in the presence of 1 µM compound.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

Buxade, M., et al, (2008). "The Mnks: MAP kinase-interacting kinases (MAP kinase signal-integrating kinases)." *Front Biosci* 13: 5359-5373.

Buxade, M., et al. (2005). "The Mnks are novel components in the control of TNF alpha biosynthesis and phosphorylate and regulate hnRNP A1." *Immunity* 23(2): 177-189.

Cherla, R. P., et al. (2006). "Shiga toxin 1-induced cytokine production is mediated by MAP kinase pathways and translation initiation factor eIF4E in the macrophage-like THP-1 cell line." *J Leukoc Biol* 79(2): 397-407.

Chrestensen, C. A., et al. (2007). "Loss of MNK function sensitizes fibroblasts to serum-withdrawal induced apoptosis." *Genes Cells* 12(10): 1133-1140.

Jauch, R., et al. (2006). "Mitogen-activated protein kinases interacting kinases are autoinhibited by a reprogrammed activation segment." *EMBO J* 25(17): 4020-4032.

Kjellerup, R. B., et al. (2008). "Pro-inflammatory cytokine release in keratinocytes is mediated through the MAPK signal-integrating kinases." *Exp Dermatol* 17(6): 498-504.

Konicek, B. W., et al. (2008). "Targeting the eIF4F translation initiation complex for cancer therapy." *Cell Cycle* 7(16): 2466-2471.

Konicek, B. W., et al. (2011). "Therapeutic inhibition of MAP kinase interacting kinase blocks eukaryotic initiation factor 4E phosphorylation and suppresses outgrowth of experimental lung metastases." *Cancer Res* 71(5): 1849-1857.

Nikolcheva, T., et al. (2002). "A translational rheostat for RFLAT-1 regulates RANTES expression in T lymphocytes." *J Clin Invest* 110(1): 119-126.

Noubade, R., et al. (2011). "Activation of p38 MAPK in CD4 T cells controls IL-17 production and autoimmune encephalomyelitis." *Blood* 118(12): 3290-3300.

Rowlett, R. M., et al. (2008). "MNK kinases regulate multiple TLR pathways and innate proinflammatatory cytokines in macrophages." *Am J Physiol Gastrointest Liver Physiol* 294(2): G452-459.

Teo, T., et al. (2015). "Pharmacologic Inhibition of MNKs in Acute Myeloid Leukemia." *Mol Pharmacol* 88(2): 380-389.

Teo, T., et al. (2015). "Pharmacologic co-inhibition of Mnks and mTORC1 synergistically suppresses proliferation and perturbs cell cycle progression in blast crisis-chronic myeloid leukemia cells." *Cancer Lett* 357(2): 612-623.

Ueda, T., et al. (2010). "Combined deficiency for MAP kinase-interacting kinase 1 and 2 (Mnk1 and Mnk2) delays tumor development." *Proc Natl Acad Sci USA* 107(32): 13984-13990.

Wendel, H. G., et al. (2007). "Dissecting eIF4E action in tumorigenesis." *Genes Dev* 21(24): 3232-3237.

TABLE 1
Activity of selected compounds according to the invention
| Structure | Example # | plc50 | | |
|---|---|---|---|---|
| | | eIF4E | MNK1 | MNK2 |
| 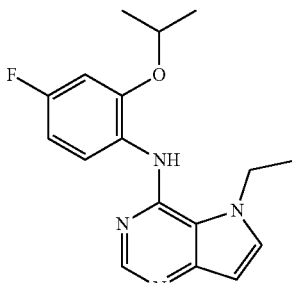 | 1 | 7.3 | 6.7 | 6.9 |
| 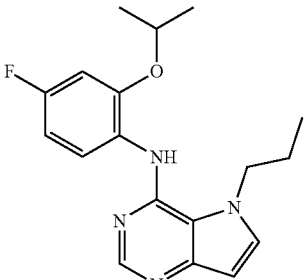 | 2 | 6.8 | 6.3 | 6.4 |
| 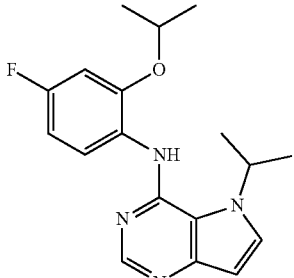 | 3 | 6.8 | 6.0 | 6.3 |
| 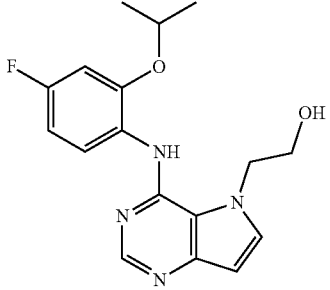 [SMILES: CC(C)Oc1cc(F)ccc1Nc1ncnc2ccn(CCO)c12] | 4 | 6.6 | 5.7 | 5.9 |
| 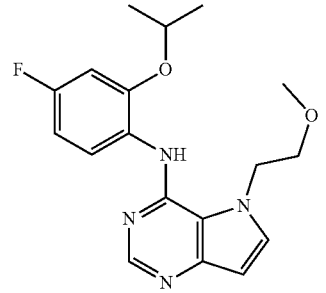 [SMILES: COCCn1ccc2ncnc(Nc3ccc(F)cc3OC(C)C)c21] | 5 | 6.0 | 5.5 | 5.7 |

TABLE 1-continued

Activity of selected compounds according to the invention

| Structure | Example # | plc50 eIF4E | MNK1 | MNK2 |
|---|---|---|---|---|
| 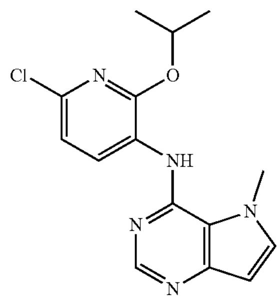 [SMILES: CC(C)Oc1nc(Cl)ccc1Nc1ncnc2ccn(C)c12] | 6 | 7.2 | 6.6 | 7.2 |
| 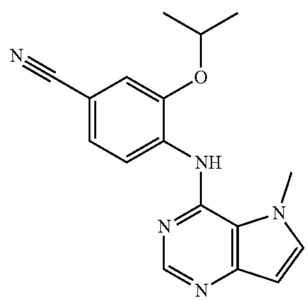 [SMILES: CC(C)Oc1cc(C#N)ccc1Nc1ncnc2ccn(C)c12] | 7 | 7.5 | 7.3 | 7.6 |
| 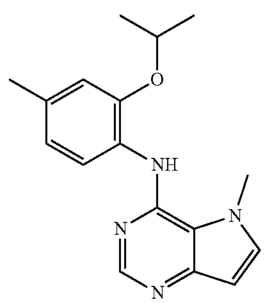 [SMILES: Cc1ccc(Nc2ncnc3ccn(C)c23)c(OC(C)C)c1] | 8 | 6.3 | 5.5 | 5.9 |
| 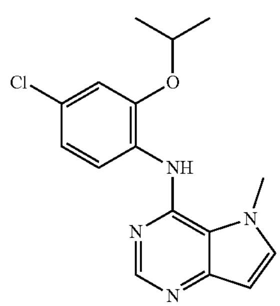 [SMILES: CC(C)Oc1cc(Cl)ccc1Nc1ncnc2ccn(C)c12] | 9 | 7.1 | 6.8 | 7.1 |
| 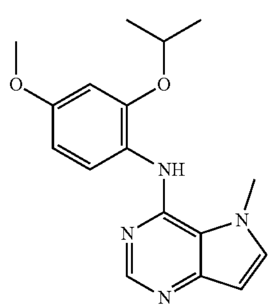 [SMILES: COc1ccc(Nc2ncnc3ccn(C)c23)c(OC(C)C)c1] | 10 | 6.7 | 5.0 | 5.9 |

TABLE 1-continued
Activity of selected compounds according to the invention
| Structure | Example # | plc50 | | |
|---|---|---|---|---|
| | | eIF4E | MNK1 | MNK2 |
| 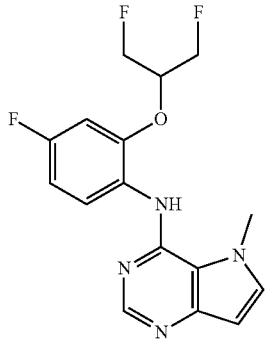 [SMILES: Cn1ccc2ncnc(Nc3ccc(F)cc3OC(CF)CF)c21] | 11 | 7.7 | 6.8 | 7.3 |
| ANO Enantiomer<br>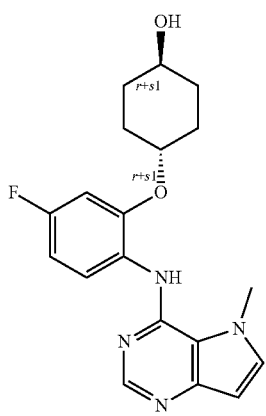 | 12 | 7.8 | 6.7 | 7.1 |
| 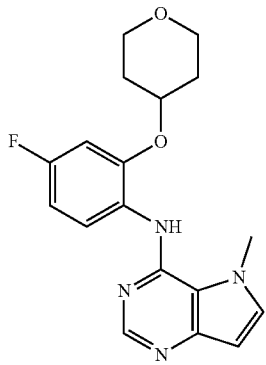 [SMILES: Cn1ccc2ncnc(Nc3ccc(F)cc3OC3CCOCC3)c21] | 13 | 7.2 | 6.5 | 6.8 |
| 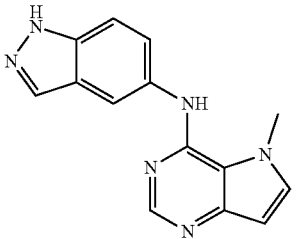 [SMILES: Cn1ccc2ncnc(Nc3ccc4[nH]ncc4c3)c21] | 14 | 6.4 | 6.6 | 6.4 |

TABLE 1-continued

Activity of selected compounds according to the invention

| Structure | Example # | pIc50 eIF4E | MNK1 | MNK2 |
|---|---|---|---|---|
| (structure) | 15 | 7.5 | 6.4 | 6,8 |
| (structure) | 16 | 7.1 | 6.6 | 6.9 |
| (structure) | 17 | 7.5 | 6.7 | 7.1 |
| (structure) | 18 | 7.7 | 7.2 | 7.5 |
| (structure) | 19 | 7.3 | 6.3 | 6.9 |
| (structure) | 20 | 6.7 | 5.5 | 6.2 |

TABLE 1-continued

Activity of selected compounds according to the invention

| Structure | Example # | pIC50 eIF4E | MNK1 | MNK2 |
|---|---|---|---|---|
| | 21 | 7.6 | 6.8 | 7.1 |
| | 22 | 7.8 | 7.0 | 7.3 |
| | 23 | 7.8 | 6.9 | 7.4 |
| | 24 | 7.1 | 6.3 | 6.7 |
| | 25 | 7.9 | 6.9 | 7.5 |

TABLE 1-continued

Activity of selected compounds according to the invention

| Structure | Example # | pIC50 eIF4E | MNK1 | MNK2 |
|---|---|---|---|---|
| (structure) | 26 | 7.8 | 7.1 | 7.5 |
| (structure) | 27 | 7.7 | 6.9 | 7.3 |
| (structure) | 28 | 7.4 | 6.4 | 6.8 |
| (structure) | 29 | 7.3 | 6.6 | 7.0 |
| (structure) | 30 | 7.2 | 6.7 | 6.9 |

TABLE 1-continued
Activity of selected compounds according to the invention
| Structure | Example # | pIc50 eIF4E | MNK1 | MNK2 |
|---|---|---|---|---|
| 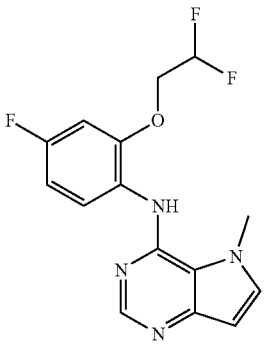 [SMILES: Cn1ccc2ncnc(Nc3ccc(F)cc3OCC(F)F)c21] | 31 | 7.3 | 6.5 | 6.8 |
| 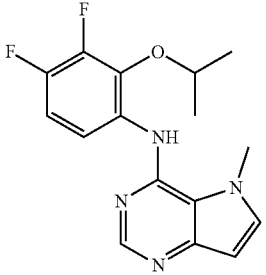 [SMILES: CC(C)Oc1c(Nc2ncnc3ccn(C)c23)ccc(F)c1F] | 32 | 6.1 | 5.7 | 6.0 |
| 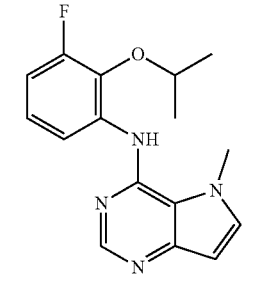 [SMILES: CC(C)Oc1c(F)cccc1Nc1ncnc2ccn(C)c12] | 33 | 7.6 | 7.0 | 7.3 |
| 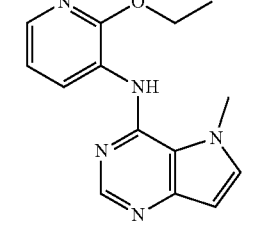 | 34 | 6.9 | 6.4 | 6.6 |
| 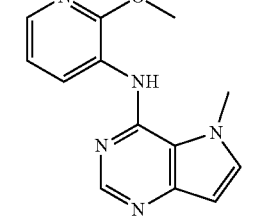 | 35 | 6.0 | 5.8 | 5.9 |

TABLE 1-continued
Activity of selected compounds according to the invention
| Structure | Example # | pIc50 | | |
|---|---|---|---|---|
| | | eIF4E | MNK1 | MNK2 |
| 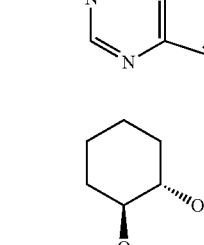 | 36 | 7.4 | 6.1 | 6.6 |
| 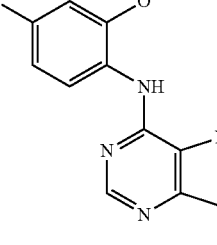 | 37 | 6.6 | 4.8 | 6.1 |
| 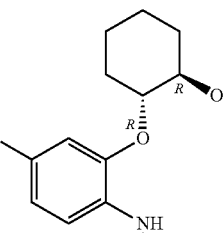 | 38 | 7.4 | 5.7 | 6.5 |
| 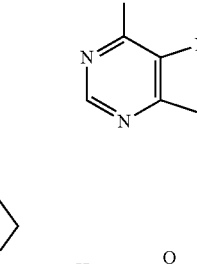 | 39 | 7.6 | 7.9 | 7.9 |

TABLE 1-continued

Activity of selected compounds according to the invention

| Structure | Example # | pIC50 | | |
|---|---|---|---|---|
| | | eIF4E | MNK1 | MNK2 |
| (structure) | 40 | 7.4 | 7.3 | 7.4 |
| (structure) | 41 | 6.7 | 7.4 | 7.4 |
| (structure) | 42 | 7.0 | 7.3 | 7.3 |
| (structure) | 43 | 6.1 | 5.9 | 6.0 |

TABLE 1-continued

Activity of selected compounds according to the invention

| Structure | Example # | plc50 eIF4E | MNK1 | MNK2 |
|---|---|---|---|---|
| 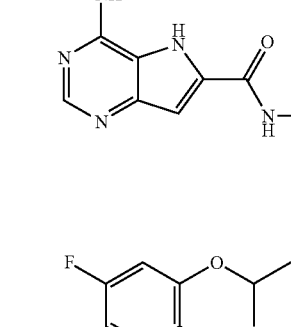 | 44 | 7.2 | 7.1 | 7.2 |
| 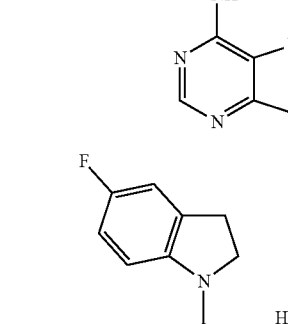 | 45 | 6.3 | 6.9 | 7.1 |
| 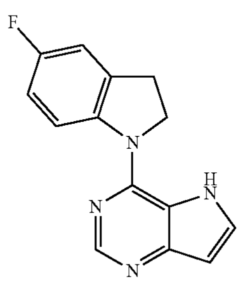 | 46 | 7.3 | 7.4 | 7.5 |

TABLE 2

Kinase Selectivity data for Example 40. Data are expressed as % inhibition of each specific kinase in the presence of 1 μM compound.

| Kinase | % Inhibition | Kinase | % Inhibition | Kinase | % Inhibition | Kinase | % Inhibition | Kinase | % Inhibition | Kinase | % Inhibition |
|---|---|---|---|---|---|---|---|---|---|---|---|
| MKNK2 | 84 | IRAK4 | 0 | PTK2 | 7 | CDK9/CCNT1 | 0 | PIK3CA | 5 | PRAK | 0 |
| STK10 | 0 | PAK2 | 0 | PTK6 | 0 | CaMK1 | 0 | ERBB4 | 0 | CDK7/CCNH/MNAT1 | 5 |
| STK17A | 2 | CSF1R | 8 | RPS6KA5 | 0 | IGF1R | 0 | MAPK8 | 0 | MARK1 | 0 |
| RPS6KA1 | 0 | CSNK1G1 | 0 | EEF2K | 0 | FGFR4 | 0 | PIP5K1A | 2 | MET | 13 |
| NUAK1 | 0 | EPHB1 | 0 | EGFR | 0 | BTK | 0 | PLK1 | 0 | ROS1 | 0 |
| MAP3K9 | 0 | KDR | 5 | FGFR1 | 0 | PAK1 | 0 | PRKAA2 | 0 | GSK3A | 0 |
| SGK1 | 0 | PIK3CB | 1 | RET | 1 | ROCK2 | 0 | RAF1 | 0 | MAP2K7 | 0 |
| DYRK2 | 8 | PIK3CD | 2 | SRC | 0 | ALK | 0 | AKT1 | 0 | FGFR2 | 0 |
| ULK2 | 0 | AKT2 | 0 | ABL2 | 0 | KIT | 2 | EPHA5 | 0 | JAK3 | 0 |
| INSR | 0 | GSK3B | 0 | DMPK | 0 | MAP2K1 | 0 | ACVR1B | 0 | MINK1 | 0 |
| TYRO3 | 0 | IKBKB | 0 | PRKCA | 5 | PIP4K2A | 7 | BLK | 4 | NEK2 | 0 |
| CAMK2B | 14 | JAK2 | 0 | ROCK1 | 0 | STK11 | 0 | FER | 0 | PRKCQ | 0 |
| TBK1 | 0 | LYN | 11 | RPS6KB1 | 0 | ABL1 | 0 | PAK7 | 0 | MST1R | 0 |
| FES | 5 | MAPK14 | 0 | EPHB4 | 2 | CHEK1 | 0 | PIK3CG | 1 | SRPK1 | 0 |
| MYLK | 0 | MAPKAPK2 | 0 | PAK4 | 0 | FLT1 | 8 | BMX | 0 | STK4 | 0 |
| MAP3K7 | 5 | MARK2 | 0 | PRKCE | 0 | PIP5K1C | 6 | FGFR3 | 10 | DDR2 | 2 |
| YES1 | 0 | PIK3C2G | 4 | LCK | 0 | AURKC | 28 | CDK1/CCNB1 | 0 | PDPK1 | 0 |
| INSRR | 0 | FYN | 0 | MTOR | 0 | CDK2/CCNA2 | 0 | CDK6/CCND3 | 0 | PRKACA | 0 |
| PIM2 | 0 | PDGFRB | 5 | NTRK1 | 0 | | | | | | |

TABLE 2-continued

Kinase Selectivity data for Example 40. Data are expressed as % inhibition of each specific kinase in the presence of 1 μM compound.

| Kinase | % Inhibition | Kinase | % Inhibition | Kinase | % Inhibition |
|---|---|---|---|---|---|
| FLT3 | 24 | TGFBR1 | 0 | AXL | 0 |
| PRKG1 | 0 | CSNK2A2 | 0 | AURKB | 14 |

The invention claimed is:

1. A compound of formula (I), or a pharmaceutically acceptable salt or ester thereof, (I)

[structure]

wherein:

$R_1$ is selected from:
  H;
  CO—$NR_8R_9$, wherein $R_8$ and $R_9$ are each independently selected from H, alkyl, cycloalkyl and mono or bicyclic heterocycloalkyl, wherein said alkyl group is optionally substituted by one or more $R_{12}$ groups, and said heterocycloalkyl is optionally substituted by one or more groups selected from $R_{10}$ and $R_{12}$; or $R_8$ and $R_9$ are linked, together with the nitrogen to which they are attached, to form a heterocycloalkyl group optionally containing one or more additional heteroatoms, and optionally substituted by one or more groups select from $R_{10}$ and $(CH_2)_m R_{12}$;

$R_2$ is selected from H and alkyl, wherein said alkyl group is optionally substituted by one or more $R_{12}$ groups;

$R_3$ is selected from alkyl, cycloalkyl and heterocycloalkyl, each of which may be optionally substituted by one or more groups selected from halo, OH and alkoxy;

$Z_1$, $Z_2$, $Z_3$ and $Z_4$ are all C;

$R_4$, $R_5$, $R_6$ and $R_7$ are each independently selected from H, alkyl, CN, $NO_2$, OH, alkoxy, NHCO-alkyl, halo and haloalkyl; or $Z_1$, $Z_3$ and $Z_4$ are all C, $Z_2$ is N, $R_5$ is absent and $R_4$, $R_6$ and $R_7$ are as defined above; or $Z_2$, $Z_3$ and $Z_4$ are all C, $Z_1$ is N, $R_4$ is absent and $R_5$, $R_6$ and $R_7$ are as defined above;

each $R_{10}$ and $R_{11}$ is independently alkyl;

each $R_{12}$ is independently selected from $CO_2R_{10}$, COOH, OH, alkoxy, haloalkyl, $NH_2$, $NHR_{10}$, $NR_{10}R_{11}$, heteroaryl and heterocycloalkyl, wherein said heterocycloalkyl is optionally further substituted by one or more $R_{10}$ groups;

$R_{13}$ is H or halo.

2. A compound according to claim 1 wherein:
$Z_1$, $Z_2$, $Z_3$ and $Z_4$ are all C; and
$R_4$, $R_5$, $R_6$ and $R_7$ are each independently selected from H, alkyl, alkoxy, and halo.

3. A compound according to claim 1 wherein
$Z_1$, $Z_2$, $Z_3$ and $Z_4$ are all C;
$R_4$, $R_5$, $R_6$ and $R_7$ are all H; or
$R_4$, $R_6$ and $R_7$ are all H and $R_5$ is halo.

4. A compound according to claim 1 wherein $Z_1$, $Z_2$, $Z_3$ and $Z_4$ are all C, $R_4$, $R_6$ and $R_7$ are all H, and $R_5$ is fluoro.

5. A compound according to claim 1 wherein $R_3$ is selected from alkyl, cyclopropyl, cyclobutyl, cyclopentyl, tetrahydrofuranyl and tetrahydropyranyl, each of which may be optionally substituted by one or more groups selected from fluoro, OH and methoxy.

6. A compound according to claim 1 wherein $R_3$ is alkyl.

7. A compound according to claim 1 wherein $R_1$ is H.

8. A compound according to claim 1 wherein $R_1$ is CO—$NR_8R_9$ and one of $R_8$ and $R_9$ is H, and the other is alkyl optionally substituted by one or more groups selected from $NR_{10}R_{11}$ and heterocycloalkyl, wherein said heterocycloalkyl is optionally substituted by one or more $R_{10}$ groups.

9. A compound according to claim 1 wherein $R_2$ is selected from H, and alkyl, wherein said alkyl is optionally substituted by one or more groups selected from OH and alkoxy.

10. A compound according to claim 1 wherein $R_2$ is selected from H, methyl, ethyl, isopropyl, hydroxyethyl and methoxyethyl.

11. A compound which is selected from the following:

1

[structure]

2

[structure]

3

[structure]

4
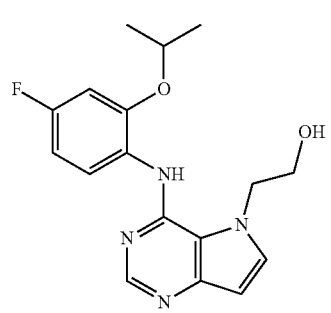
5
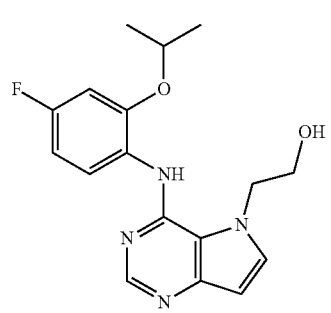
6
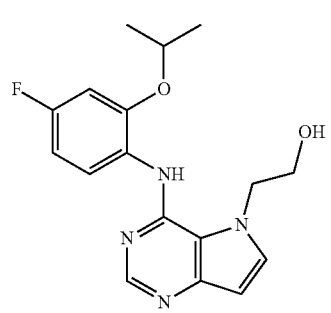
7
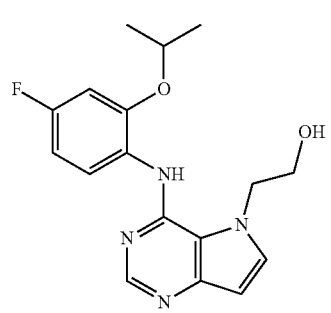
8
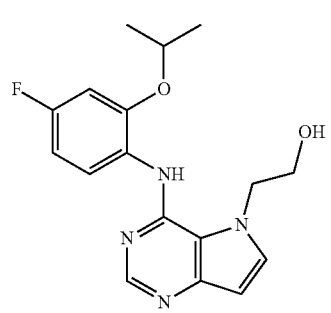
9
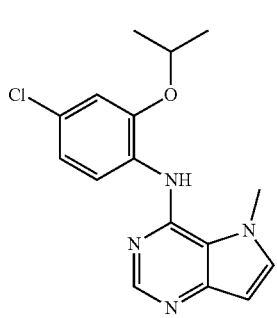
10
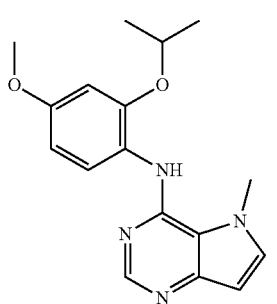
11
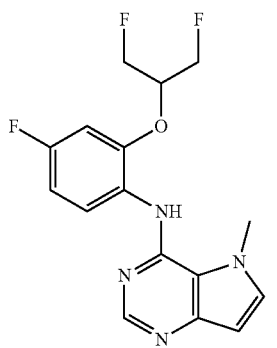
12
AND Enantiomer
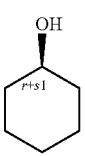
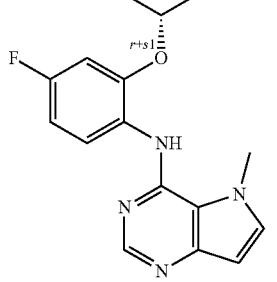

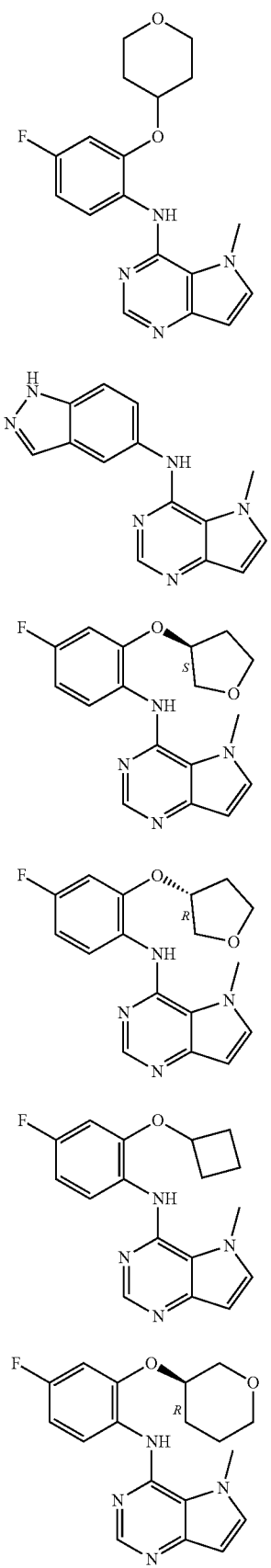
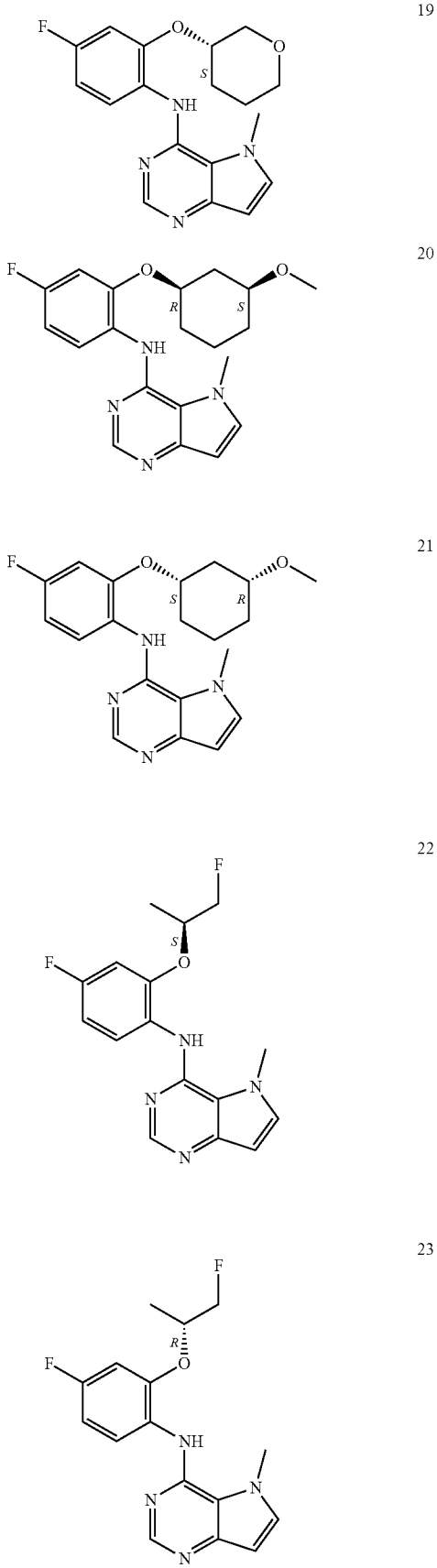

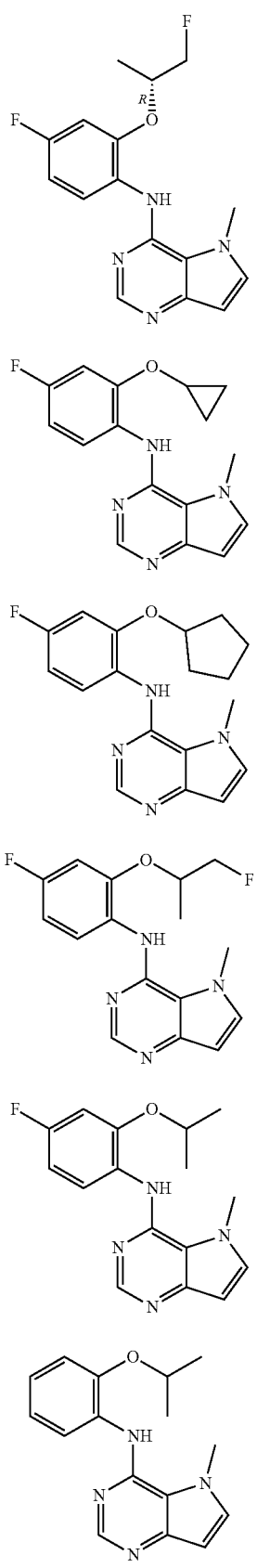
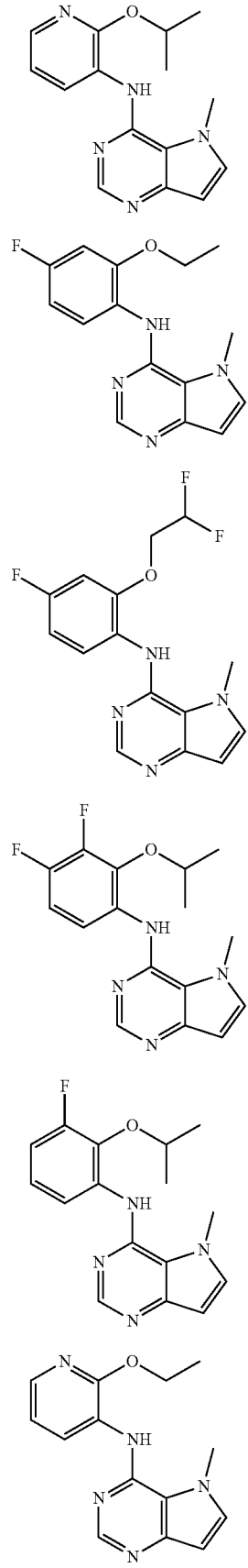

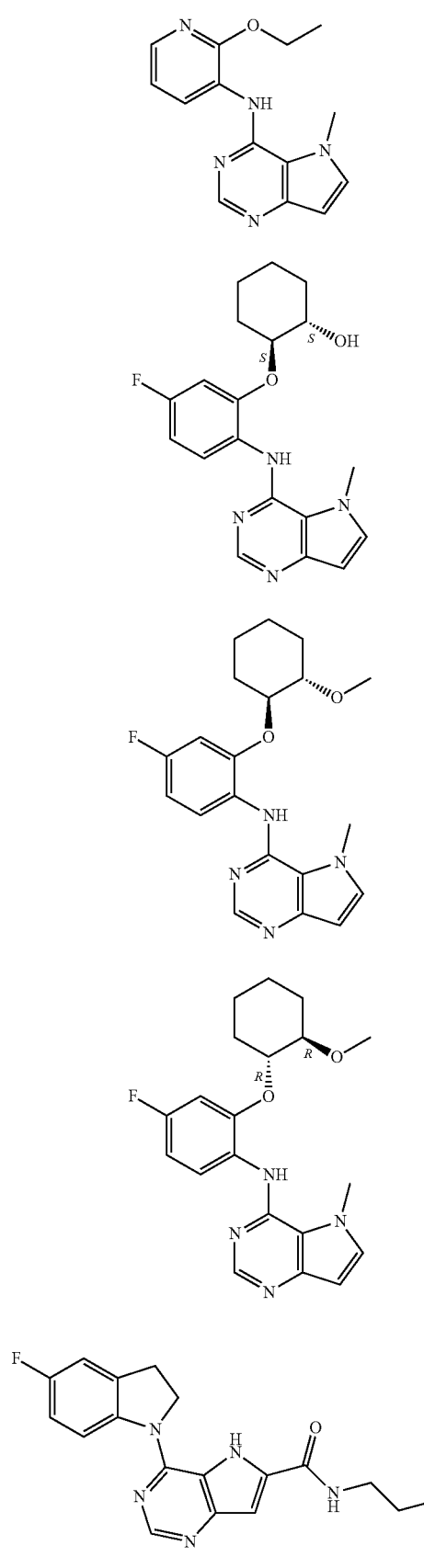
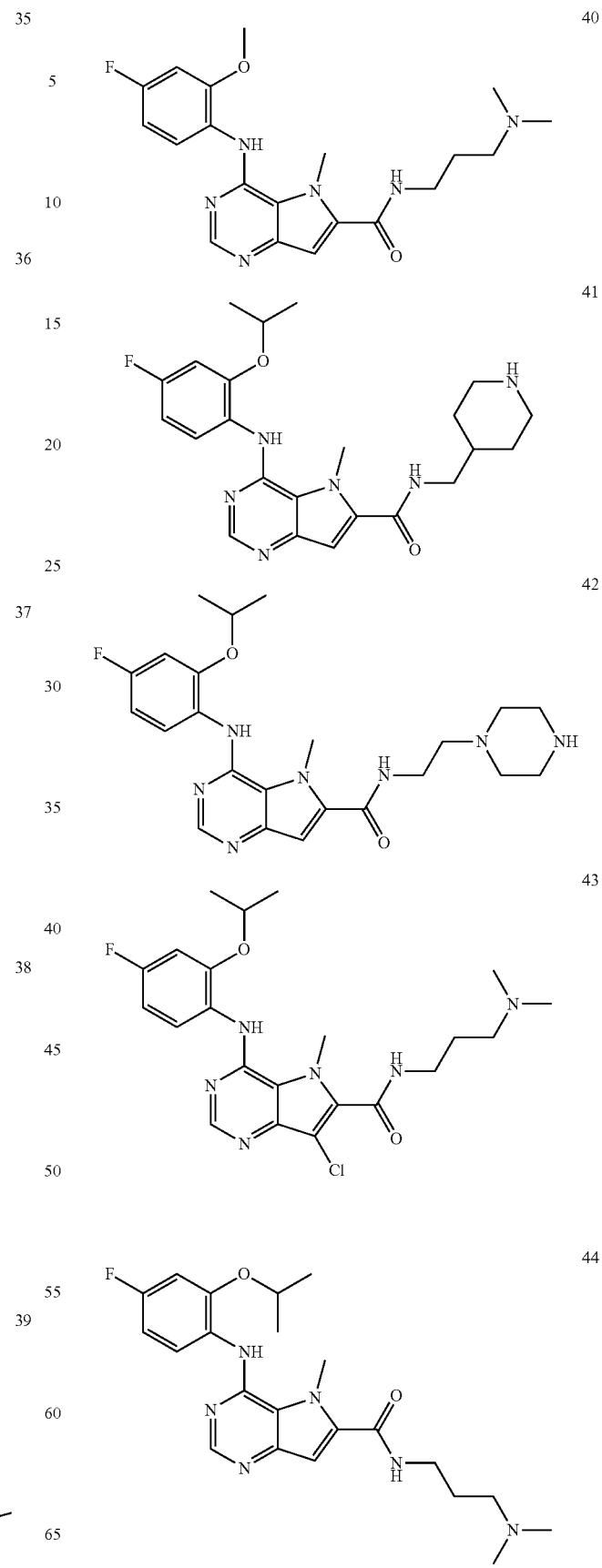

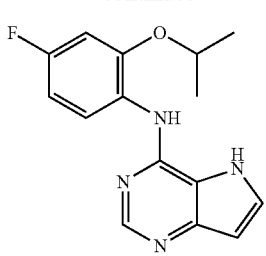 [SMILES: CC(C)Oc1cc(F)ccc1Nc1ncnc2cc[nH]c12]

and pharmaceutically acceptable salts or esters thereof.

12. A pharmaceutical composition comprising a compound according to claim 1 and a pharmaceutically acceptable carrier, diluent or excipient.

13. A method of treating a proliferative disorder selected from a hematological tumour, a solid tumour and/or metastases a neurodegenerative disorder or an inappropriate cellular inflammatory response, thereof, comprising administering to a subject in need thereof a compound of claim 1.

14. A compound according to claim 1, wherein the compound of formula (I) is or a pharmaceutically acceptable salt or ester thereof.

* * * * *